US008005284B2

(12) United States Patent
Sakaguchi et al.

(10) Patent No.: US 8,005,284 B2
(45) Date of Patent: Aug. 23, 2011

(54) THREE DIMENSIONAL IMAGE PROCESSING APPARATUS AND X-RAY DIAGNOSIS APPARATUS

(75) Inventors: Takuya Sakaguchi, Shioya-gun (JP); Michael D. Silver, Northbrook, IL (US)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 1120 days.

(21) Appl. No.: 11/608,005

(22) Filed: Dec. 7, 2006

(65) Prior Publication Data

US 2008/0137934 A1 Jun. 12, 2008

(51) Int. Cl.
*G06T 15/00* (2011.01)

(52) U.S. Cl. ........................................ 382/131; 382/154

(58) Field of Classification Search .................. None
See application file for complete search history.

(56) References Cited

U.S. PATENT DOCUMENTS

| 2005/0089136 | A1 | 4/2005 | Toth et al. |
| 2005/0220264 | A1 | 10/2005 | Homegger |
| 2005/0226485 | A1 | 10/2005 | Boese |
| 2005/0286679 | A1 | 12/2005 | Sakaguchi et al. |
| 2006/0210019 | A1* | 9/2006 | Rasche et al. .................. 378/62 |
| 2006/0210147 | A1 | 9/2006 | Sakaguchi |

FOREIGN PATENT DOCUMENTS

WO  WO 2004/114221 A1  12/2004

OTHER PUBLICATIONS

U.S. Appl. No. 11/844,048, filed Aug. 23, 2007, Sakaguchi, et al.
U.S. Appl. No. 12/574,305, filed Oct. 6, 2009, Sakaguchi.
U.S. Appl. No. 12/578,862, filed Oct. 14, 2009, Sakaguchi.
U.S. Appl. No. 11/680,122, filed Feb. 28, 2007, Sakaguchi.
U.S. Appl. No. 12/756,553, filed Apr. 8, 2010, Ohishi.
B. Movassaghi, et al., "3D coronary reconstruction from calibrated motion-compensated 2D projections based on semi-automated feature point detection", Proceedings of SPIE vol. 5370, 2004, pp. 1943-1950.

* cited by examiner

*Primary Examiner* — Brian P Werner
(74) *Attorney, Agent, or Firm* — Oblon, Spivak, McClelland, Maier & Neustadt, L.L.P.

(57) ABSTRACT

A three dimensional image processing apparatus includes a feature point designation unit which designates feature points on at least two selected images selected from a plurality of images in different radiographing directions, a three dimensional position calculation unit which calculates a three dimensional position associated with a feature point, a two dimensional position calculation unit which calculates the two dimensional position of a feature point on an unselected image on the basis of the calculated three dimensional position of the feature point, a feature point extraction unit which extracts a feature point from an unselected image, a positional shift calculation unit which calculates a positional shift of the two dimensional position of the extracted feature point with respect to the calculated two dimensional position of the feature point, and a correction unit which corrects the position of the unselected image on the basis of the calculated positional shift.

24 Claims, 33 Drawing Sheets

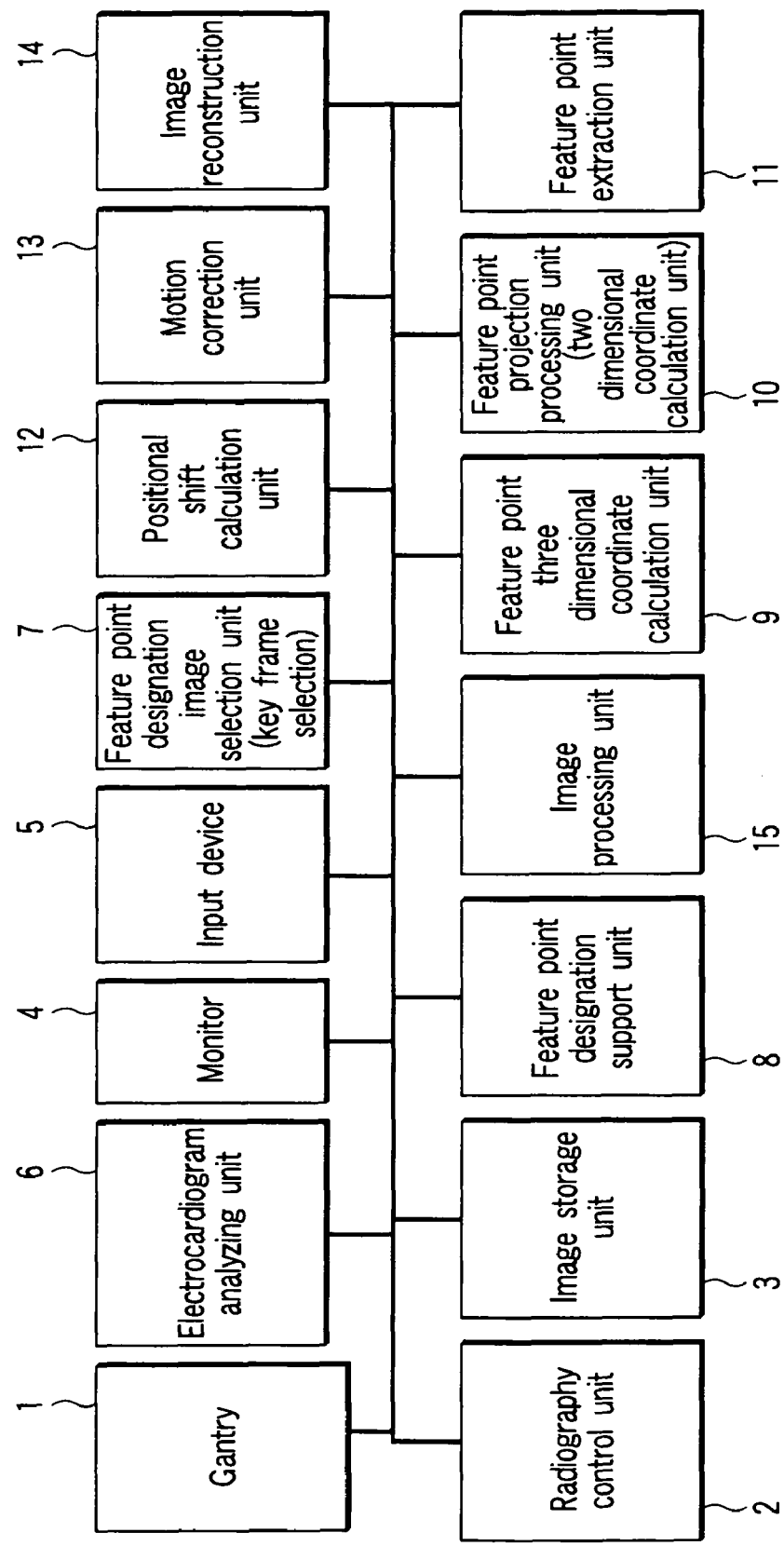
F I G. 1

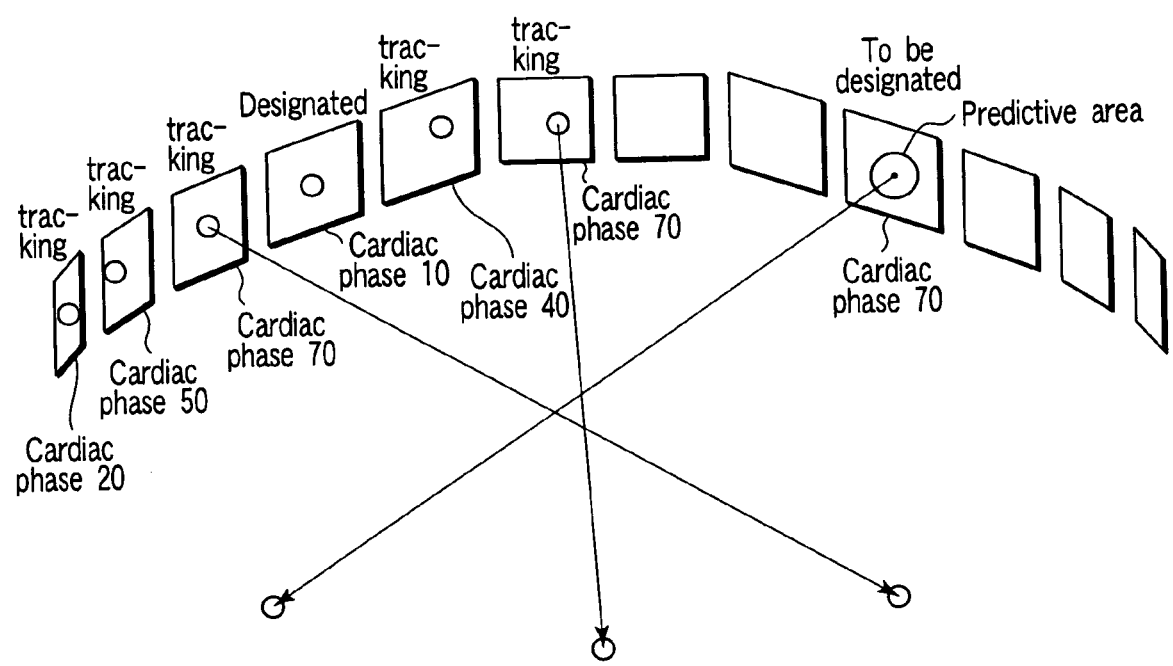
F I G. 17

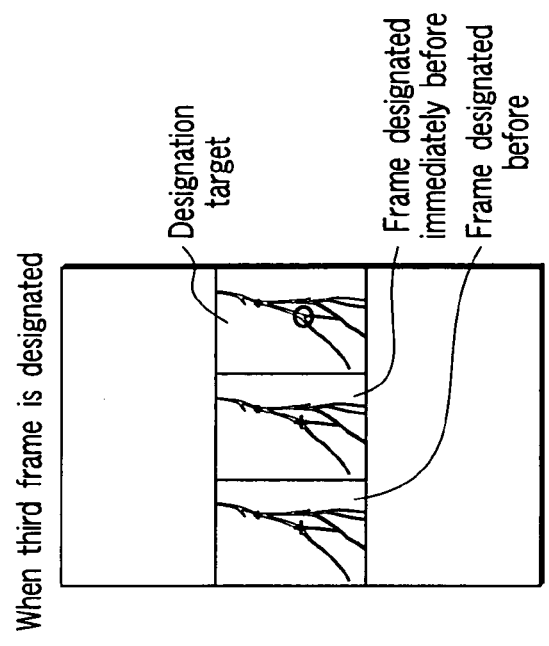
FIG. 24A When first frame is designated
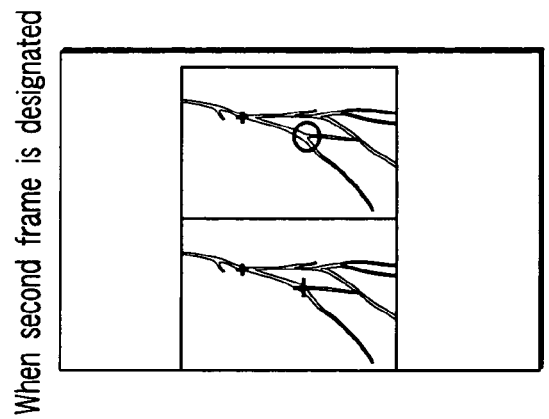
FIG. 24B When second frame is designated
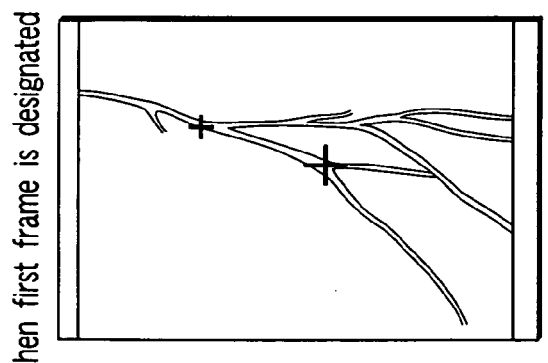
FIG. 24C When third frame is designated
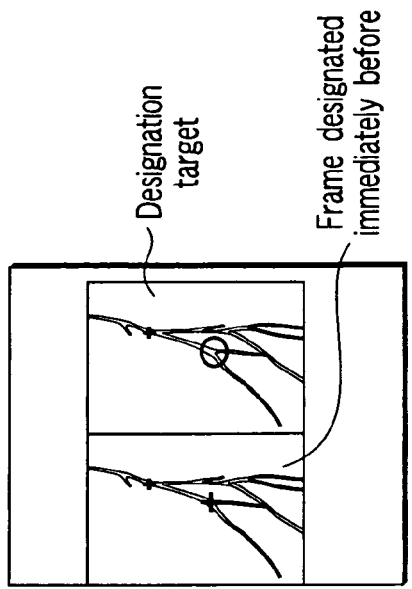
FIG. 25A
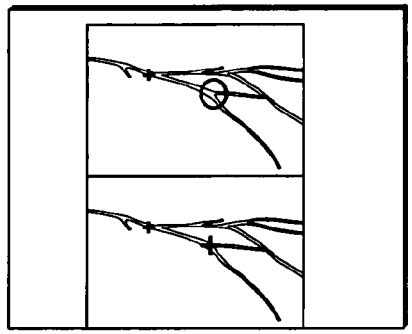
FIG. 25B
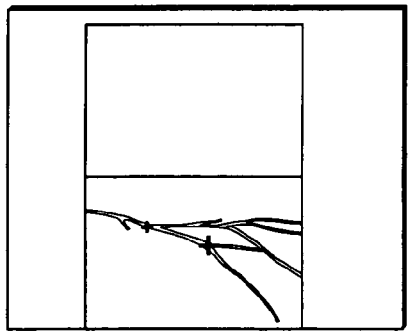
FIG. 25C ● Method of displaying key frames side by side (always three windows)

When first frame is designated

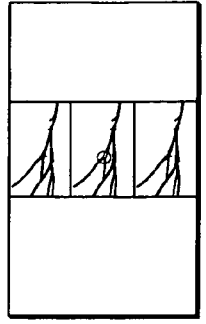

FIG. 26A

When second frame is designated

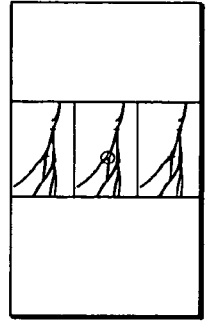

FIG. 26B

When third frame is designated

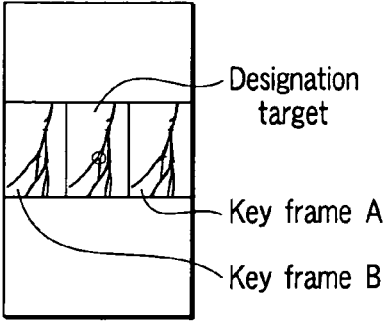

FIG. 26C

— Designation target
— Key frame A
— Key frame B

● Method of increasing number of thumbnail windows

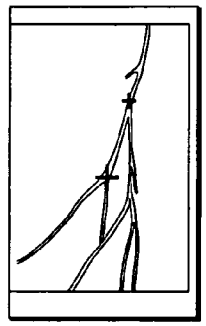

FIG. 27A

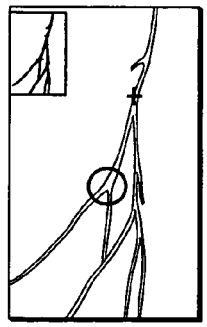

FIG. 27B

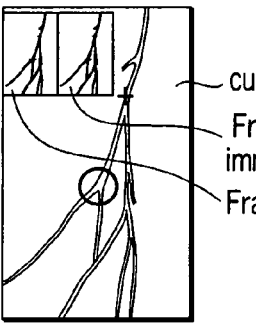

FIG. 27C

— curre
— Frame designated immediately before
— Frame designated before

● Method of enlarging thumbnails and increasing number of windows to be displayed

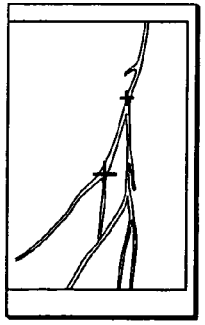

FIG. 28A

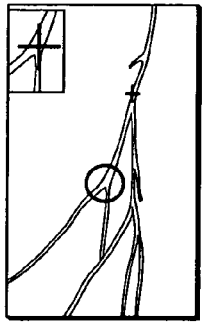

FIG. 28B

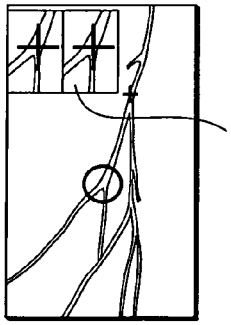

FIG. 28C

— Enlarged image

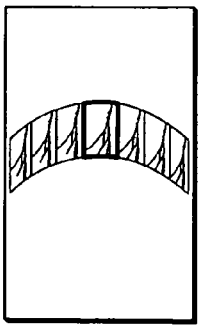

FIG. 28D

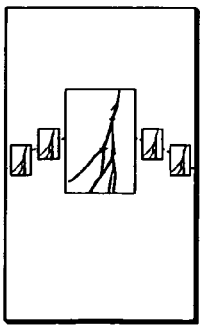

FIG. 28E

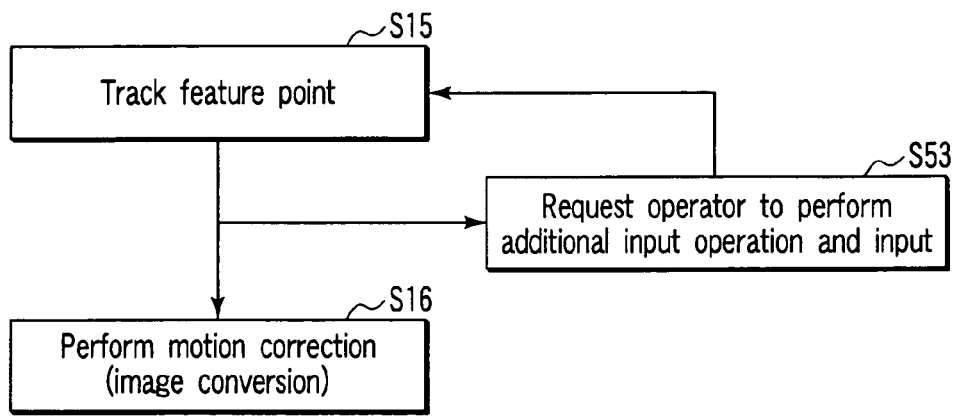
F I G. 44
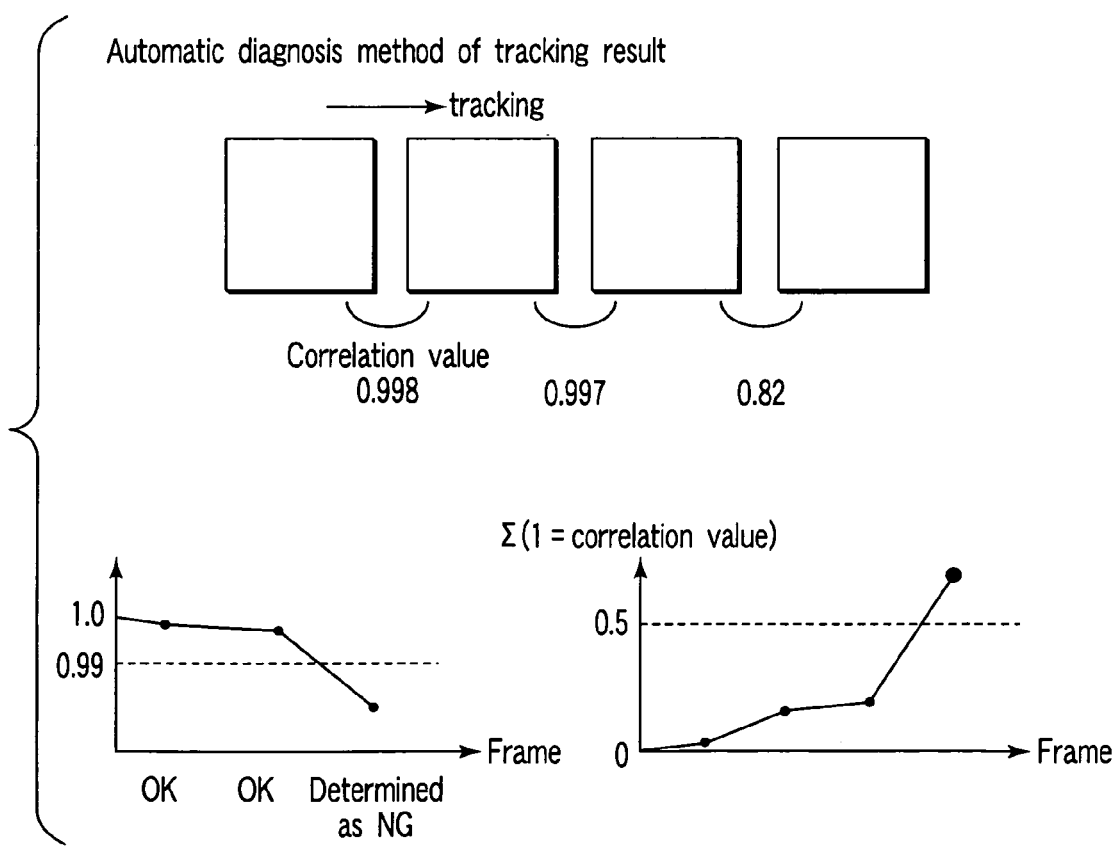
F I G. 45

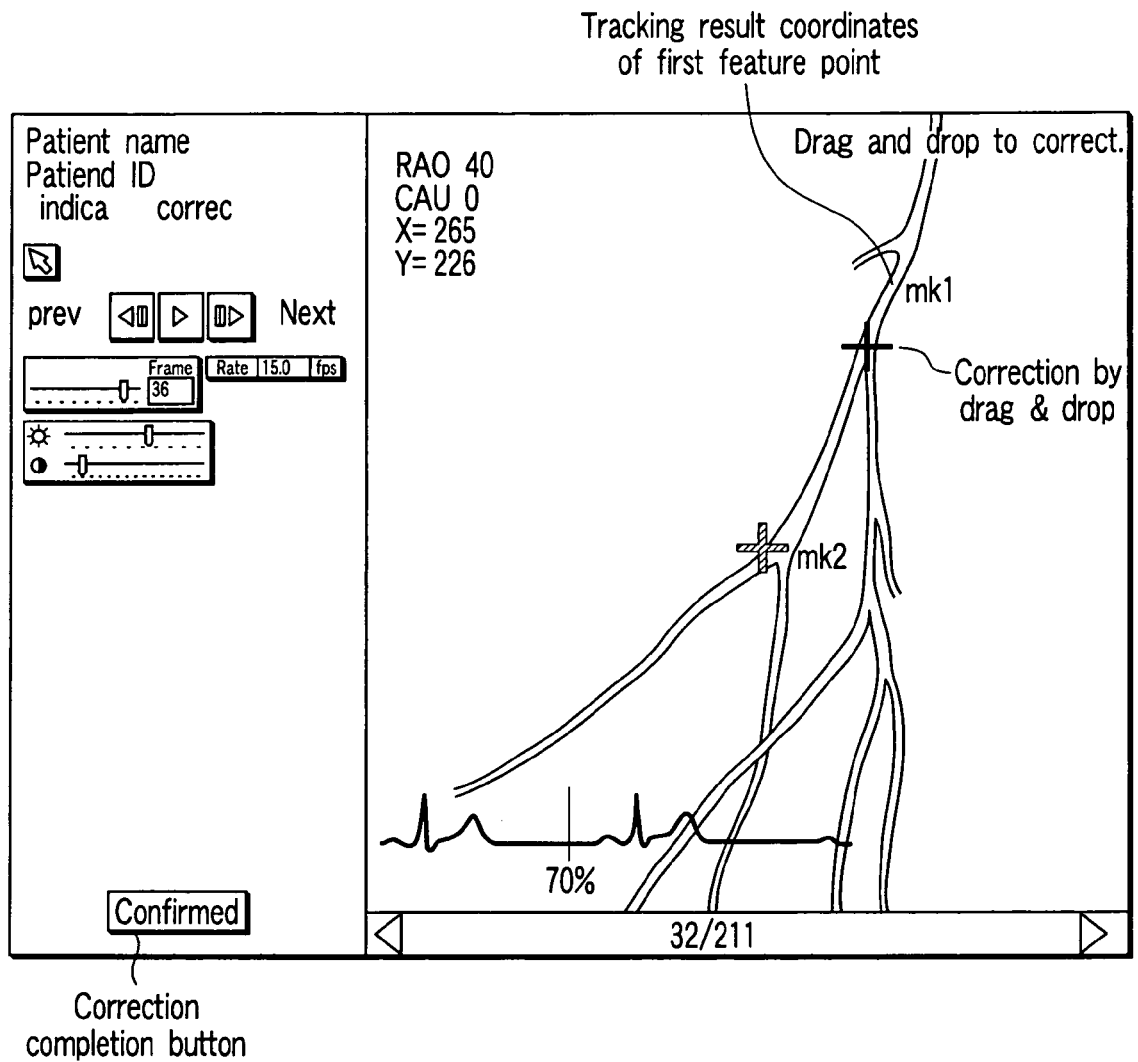
F I G. 47

Example of margin setting

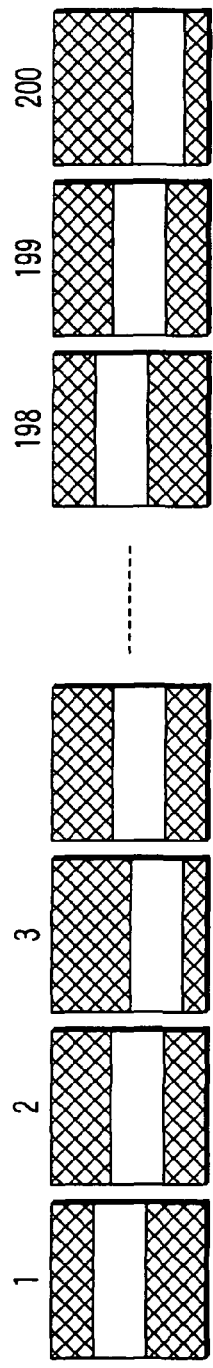
FIG. 57 Example 1 of narrowing range determination method = changing range for each frame and equalizing stop plan line with actual narrowing range for each frame
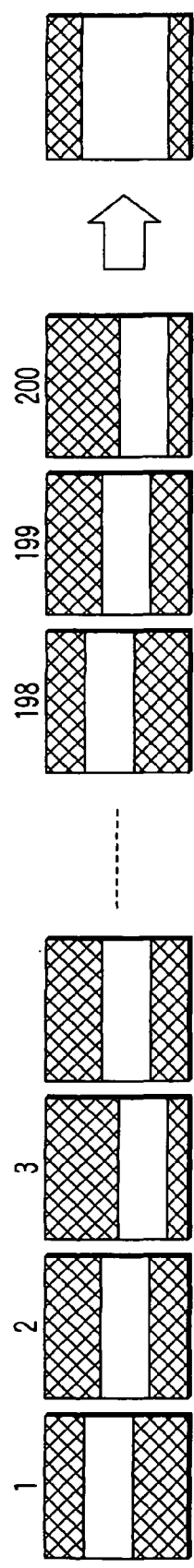
FIG. 58 Example 2 of narrowing range determination method = changing range for each frame and set narrowing range in accordance with maximum and minimum values of stop plan line

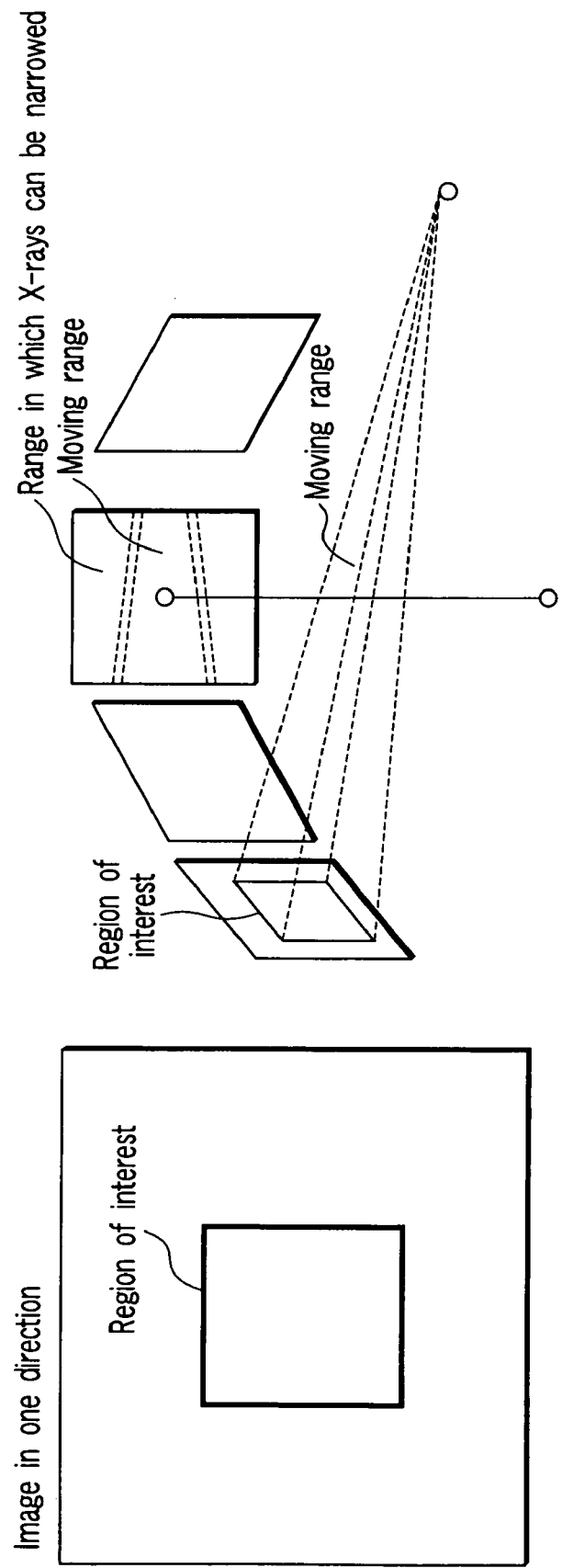
F I G. 59

THREE DIMENSIONAL IMAGE PROCESSING APPARATUS AND X-RAY DIAGNOSIS APPARATUS

BACKGROUND OF THE INVENTION

1. Field of the Invention

The present invention relates to a three dimensional image processing apparatus which reconstructs a three dimensional image from a plurality of X-ray images obtained in different radiographing directions and an X-ray diagnosis apparatus.

2. Description of the Related Art

Recently, studies have been made on a technique of reconstructing a three dimensional image from a plurality of X-ray images obtained in different radiographing directions using the same technique as that for X-ray computed tomography. For example, this technique is useful for cardiovascular examination. Since heart blood vessels, move in accordance with heart beating motion, motion artifacts occur.

In order to solve this problem, it is necessary to correct the motions of coronary vessels. In addition, since the motion of the heart is not constant, motion correction based on a model is not sufficient, and it is necessary to perform motion correction based on an actual image.

For the motion correction of heart blood vessels based on an actual image, a region of interest should be corrected region by region because heart motion is different region by region. One method is to find such region of interest automatically by a computer. However, errors may occur.

BRIEF SUMMARY OF THE INVENTION

It is an object of the present invention to improve the image quality of a three dimensional image reconstructed from X-ray images in many directions.

According to a aspect of the present invention, there is provided a three dimensional image processing apparatus comprising a storage unit which stores data of a plurality of images in different radiographing directions, a feature point designation unit which designates, with operation by an operator, at least one feature point on at least two selected images selected from the plurality of images, a three dimensional position calculation unit which calculates a three dimensional position associated with the feature point on the basis of a radiographing direction corresponding to the selected image and a two dimensional position of the designated feature point on the selected image, a two dimensional position calculation unit which calculates a two dimensional position of the feature point on an unselected image of the plurality of images on the basis of a radiographing direction corresponding to the unselected image and the calculated three dimensional position of the feature point, a feature point extraction unit which extracts a feature point from the unselected image, a positional shift calculation unit which calculates a positional shift of the two dimensional position of the extracted feature point with respect to the calculated two dimensional position of the feature point, a correction unit which corrects the position of the unselected image on the basis of the calculated positional shift, and an image reconstruction unit which reconstructs a three dimensional image on the basis of the selected image and the corrected unselected image.

According to a second aspect of the present invention, there is provided a three dimensional image processing apparatus comprising a storage unit which stores data of a plurality of images in different radiographing directions, a feature point designation unit which designates, with operation by an operator, at least one feature point on at least two selected images selected from the plurality of images, a three dimensional position calculation unit which calculates a three dimensional position associated with the feature point on the basis of a radiographing direction corresponding to the selected image and a two dimensional position of the designated feature point on the selected image, a two dimensional position calculation unit which calculates a two dimensional position of the feature point on an unselected image of the plurality of images on the basis of a radiographing direction corresponding to the unselected image and the calculated three dimensional position of the feature point, a feature point extraction unit which extracts a feature point from the unselected image, a display unit which displays a feature point extraction result obtained by the feature point extraction unit, a positional shift calculation unit which calculates a positional shift of the two dimensional position of the extracted feature point with respect to the calculated two dimensional position of the feature point, a correction unit which corrects the position of the unselected image on the basis of the calculated positional shift, and an image reconstruction unit which reconstructs a three dimensional image on the basis of the selected image and the corrected unselected image.

According to a third aspect of the present invention, there is provided an X-ray diagnosis apparatus comprising an X-ray tube which generates X-rays, an x-ray collimator which variably narrows X-rays from the X-ray tube, an X-ray detector which detects X-rays transmitted through a subject, a rotating mechanism which rotates the X-ray tube around the subject together with the X-ray detector, an image reconstruction unit which reconstructs a three dimensional image on the basis of a plurality of image data in different radiographing directions in which radiography is repeated while the X-ray tube and the X-ray detector rotate around the subject, a region-of-interest setting unit which sets a region of interest on an image of at least one frame by the X-ray detector, and a control unit which controls an aperture of the x-ray collimator on the basis of the set region of interest.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out herein after.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 1 is a view showing the arrangement of a three dimensional image processing apparatus according to this embodiment;

FIG. 17 is a view showing another example of determination of a predictive area in step S25 in FIG. 6;

FIG. 24A is a view showing an example of a window in the step of designating a feature point on the image of the first frame in this embodiment;

FIG. 24B is a view showing an example of a window in the step of designating a feature point on the image of the second frame in this embodiment;

FIG. 24C is a view showing an example of a window in the step of designating a feature point on the image of the third frame in this embodiment;

FIG. 25A is a view showing another example of the window in the step of designating a feature point on the image of the first frame in this embodiment;

FIG. 25B is a view showing another example of the window in the step of designating a feature point on the image of the second frame in this embodiment;

FIG. 25C is a view showing another example of the window in the step of designating a feature point on the image of the third frame in this embodiment;

FIG. 26A is a view showing another example of the window in the step of designating a feature point on the image of the first frame in this embodiment;

FIG. 26B is a view showing another example of the window in the step of designating a feature point on the image of the second frame in this embodiment;

FIG. 26C is a view showing another example of the window in the step of designating a feature point on the image of the third frame in this embodiment;

FIG. 27A is a view showing another example of the window in the step of designating a feature point on the image of the first frame in this embodiment;

FIG. 27B is a view showing another example of the window in the step of designating a feature point on the image of the second frame in this embodiment;

FIG. 27C is a view showing another example of the window in the step of designating a feature point on the image of the third frame in this embodiment;

FIG. 28A is a view showing another example of the window in the step of designating a feature point on the image of the first frame in this embodiment;

FIG. 28B is a view showing another example of the window in the step of designating a feature point on the image of the second frame in this embodiment;

FIG. 28C is a view showing another example of the window in the step of designating a feature point on the image of the third frame in this embodiment;

FIG. 28D is a view showing an example of scroll display of an image in this embodiment;

FIG. 28E is a view showing another example of scroll display of an image in this embodiment;

FIG. 44 is a view showing automatic determination processing for the tracking result in FIG. 30;

FIG. 45 is a view showing a concrete example of automatic determination processing for a tracking result in FIG. 44;

FIG. 47 is a view showing a concrete display example for correcting the tracking result in FIG. 30;

FIG. 57 is a view showing the details of a stop area determined for each frame in step S64 in FIG. 55;

FIG. 58 is a view showing the details of a stop area common to frames which is determined in step S64 in FIG. 55; and FIG. 59 is a view for explaining another method of setting a region of interest in FIG. 53.

DETAILED DESCRIPTION OF THE INVENTION

A three dimensional image processing apparatus and an X-ray diagnosis apparatus according to an embodiment of the present invention will be described below with reference to the views of the accompanying drawing. The three dimensional image processing apparatus will be described as an apparatus incorporated in a radiographic apparatus. Obviously, however, this apparatus may be singly used. Alternatively, the three dimensional image processing apparatus may be implemented as a program for causing a computer to implement the function of the apparatus, or can be provided as a computer-readable storage medium which stores the program. Although a target object will be described as a heart blood vessel, three dimensional image processing can be applied to even an organ other than a heart blood vessel or a device to be inserted in the body of a subject, e.g., a stent.

Figure 2:
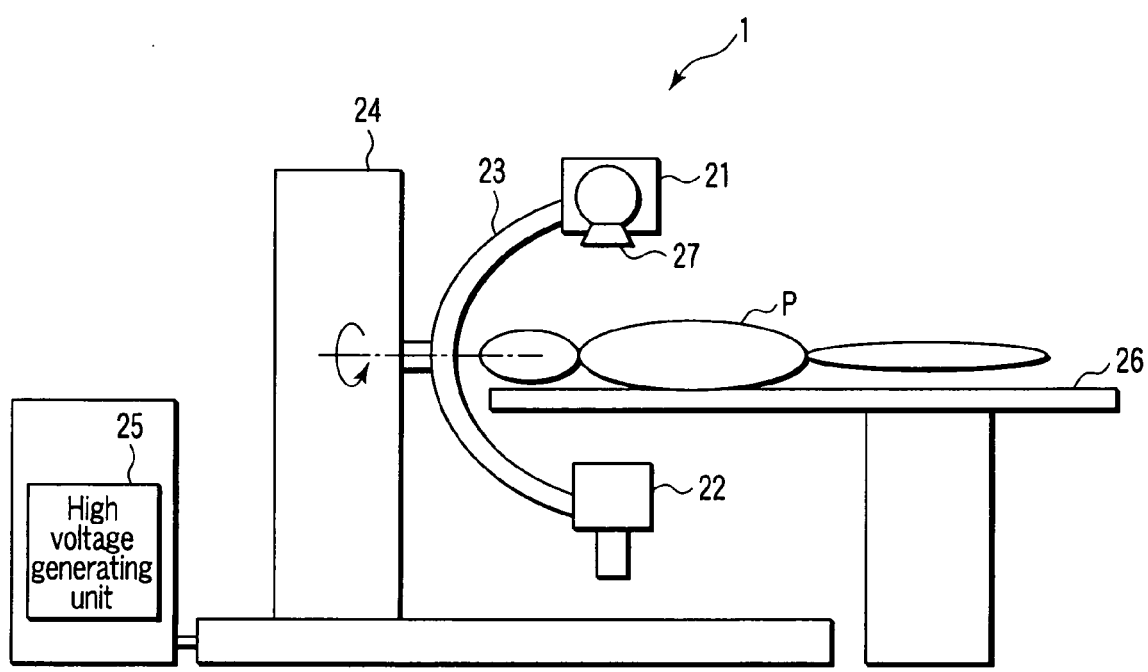
FIG. 2 is a view showing the structure of a gantry in FIG. 1.

FIG. 1 shows a radiographic apparatus incorporating a three dimensional image processing apparatus according to this embodiment. As shown in FIG. 2, a gantry 1 includes an X-ray tube 21 and an X-ray detector 22. A high voltage generating unit 25 generates a high voltage to be applied between the electrodes of the X-ray tube 21. Upon receiving the high voltage, the X-ray tube 21 generates X-rays. The X-ray detector 22 is typically a solid flat panel detector comprising a two dimensional array of a plurality of detection elements (pixels) which directly or indirectly convert incident X-rays into electric charges. The X-ray tube 21 is mounted on, for example, one end of a floor type C-arm 23. The X-ray detector 22 is mounted on the other end of the C-arm 23. The X-ray detector 22 faces the X-ray tube 21 through a subject P placed on a bed 26. The C-arm 23 is rotatably supported on a stand 24. Repeating radiography while rotating the C-arm 23 makes it possible to acquire X-ray images (transmission images) in many directions which are required for three dimensional image reconstruction.

A radiography control unit 2 controls the application of high voltages from the high voltage generating unit 25 to the X-ray tube 21 and reading of signals from the X-ray detector 22, thereby executing radiographing operation and generating X-ray image (projection image) data. This apparatus includes an image storage unit 3 to store this X-ray image data. Although not shown, an electrocardiograph is attached to the subject P to acquire the electrocardiograms of the subject P. An electrocardiogram analyzing unit 6 identifies a cardiac phase when an X-ray image is captured from an electrocardiogram. A cardiac phase represents a time point between R waves, and is generally expressed in percentage. The data of a cardiac phase at the time of radiography is associated with each X-ray image. The apparatus includes an image reconstruction unit 14 for reconstructing three dimensional image data from X-ray images in many directions which are stored in the image storage unit 3.

A system for correcting the positional shift of a subject image in the image coordinate system between X-ray images in many directions due to respiration, cardiac beats, and the like comprises a monitor 4 for displaying X-ray images, an input device 5 for feature point designating operation and the like, a feature point designation image selection unit 7, a feature point designation support unit 8, a feature point three dimensional coordinate calculation unit 9, a feature point projection processing unit 10, a feature point extraction unit (tracking unit) 11, a positional shift calculation unit 12, a motion correction unit 13, and an image processing unit 15.

The feature point designation image selection unit 7 selects the data of X-ray images (to be referred to as key images) of at least two frames corresponding to the same cardiac phase from X-ray images in many directions which are stored in the image storage unit 3. Under initial conditions, for example, the feature point designation image selection unit 7 selects the data of X-ray images of five frames acquired at end-diastolic as key images. The image processing unit 15 performs image processing for the key images, as needed. The feature point designation support unit 8 then displays the images on the monitor 4. The support information generated by the feature point designation support unit 8 is superimposed and displayed on each key image. Although described in detail later, support information is information for supporting the operator to designate an anatomically characteristic point (feature point) on each key image through the input device 5. More specifically, this information serves as a predictive area in which a feature point is predicted to be located on an undesignated key image by geometric calculation from the two dimensional coordinates of a feature point on a designated key image and the radiographing direction.

Figure 3:
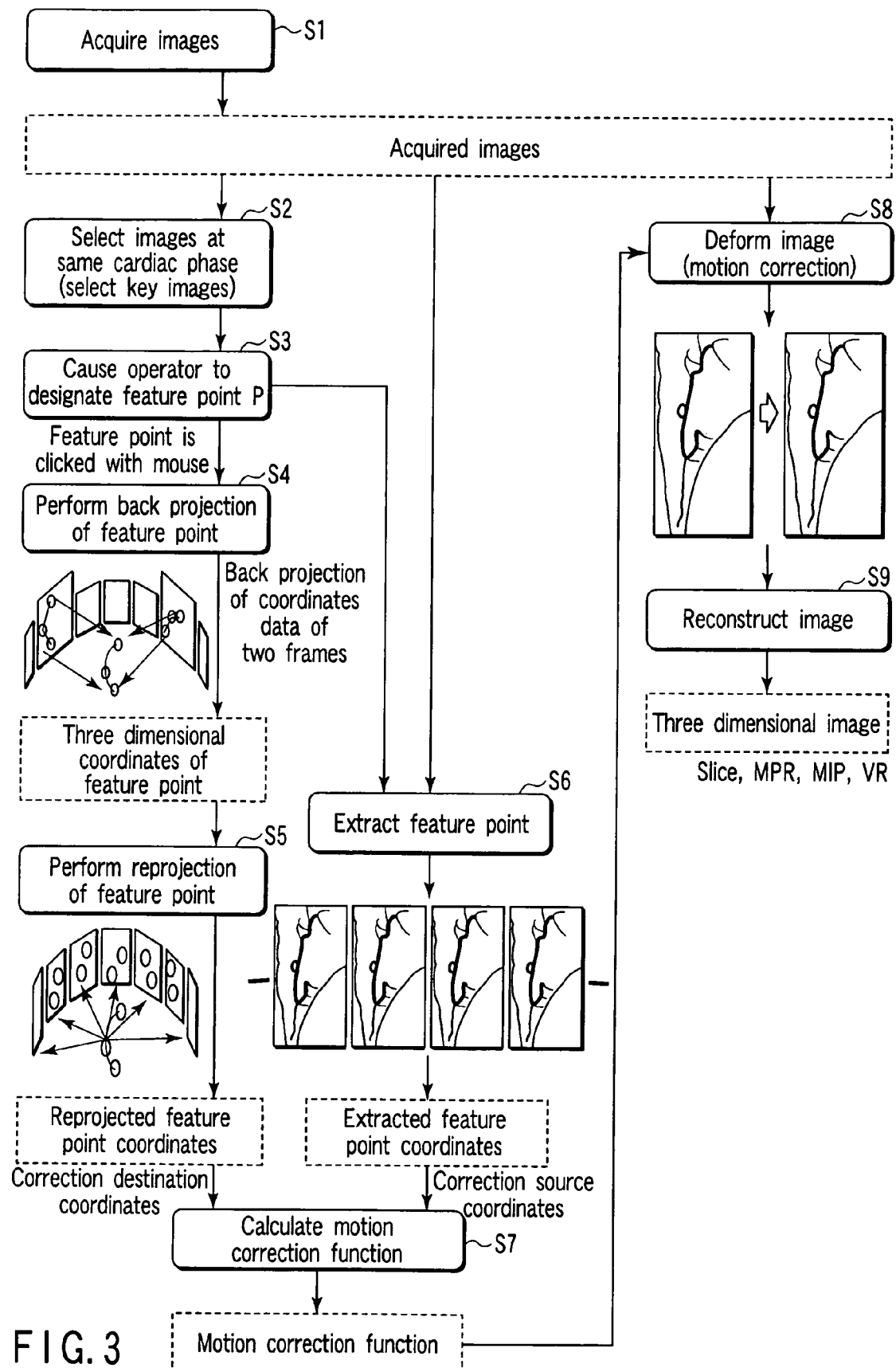
FIG. 3 is a view showing an outline of the overall operation of this embodiment.
Figure 4:
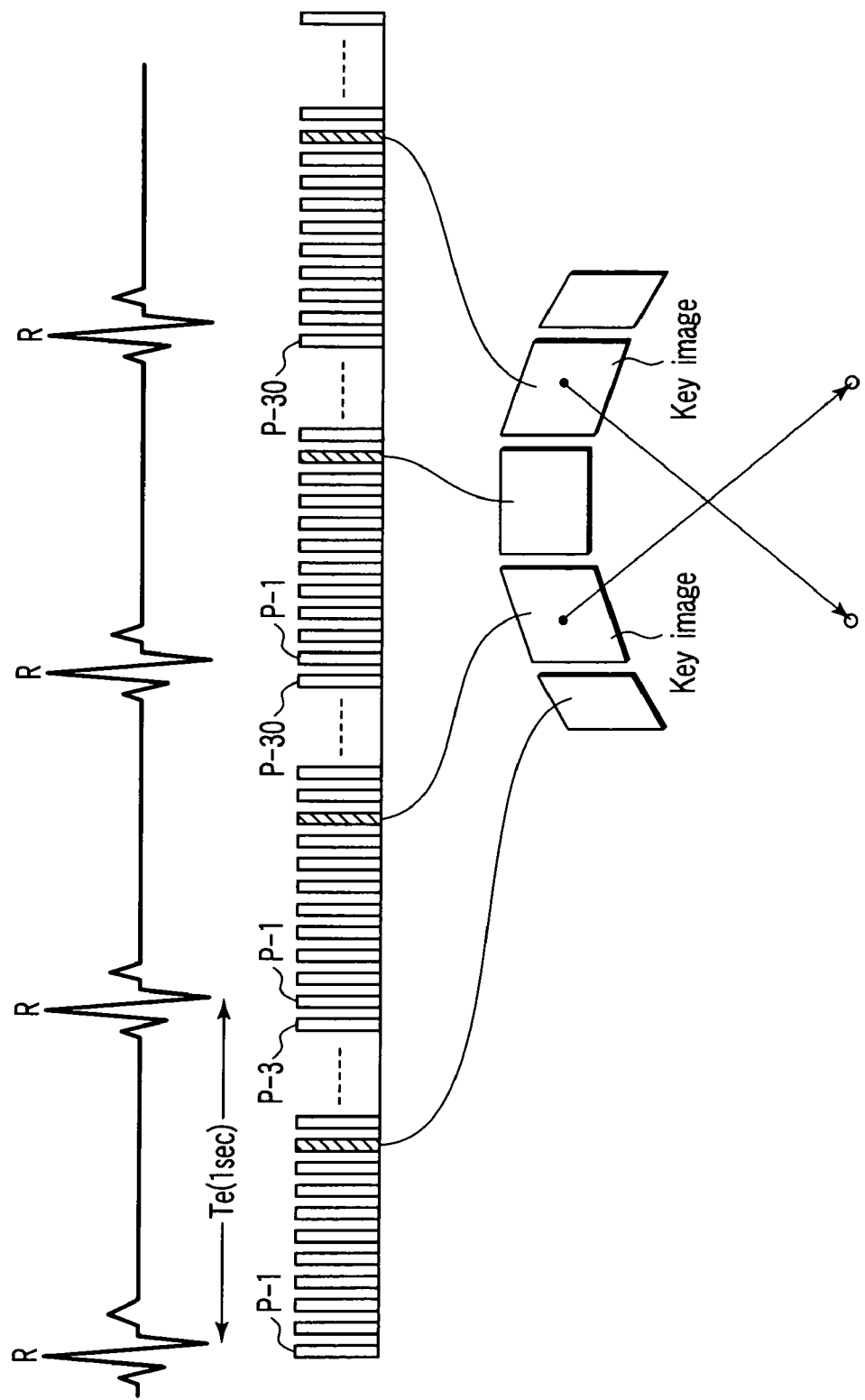
FIG. 4 is a supplementary view for explaining step S2 in FIG. 3.
Figure 5:
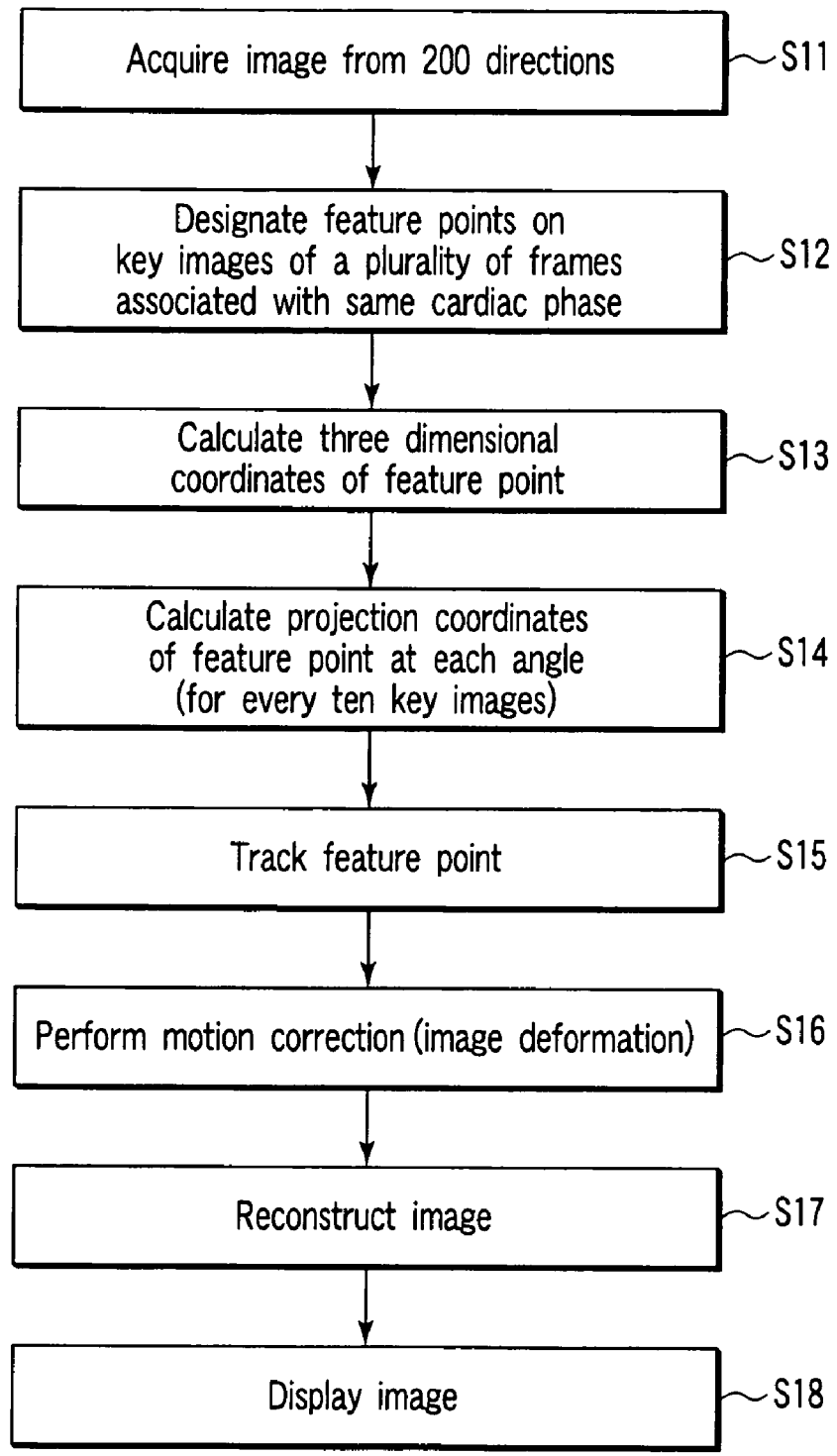
FIG. 5 is a flowchart corresponding to FIG. 3.

The feature point three dimensional coordinate calculation unit 9 calculates the three dimensional coordinates (three dimensional position) of a feature point by geometric calculation on the basis of the two dimensional coordinates of a plurality of feature points designated on a plurality of key images and the respective radiographing directions. The feature point projection processing unit 10 calculates the two dimensional coordinates of a feature point projected on each non-key image on the basis of the calculated three dimensional coordinates of the feature point and the radiographing directions of the remaining images (non-key images) other than the key images. The feature point extraction unit 11 extracts feature points from non-key images. The positional shift calculation unit 12 calculates the positional shifts of the two dimensional coordinates of the feature points extracted from the non-key images by the feature point extraction unit 11 with respective to the two dimensional coordinates of the feature points calculated by the feature point projection processing unit 10. The motion correction unit 13 corrects the positions of the non-key images in accordance with the positional shifts calculated by the positional shift calculation unit 12. The image reconstruction unit 14 reconstructs three dimensional image data on the basis of the key images and the position-corrected non-key images FIG. 3 shows an outline of the overall operation between image acquisition and the generation of a three dimensional image. FIG. 5 is a flowchart showing a processing procedure in the three dimensional image processing apparatus according to this embodiment. The C-arm 23 continuously rotates under the control of the radiography control unit 2, and radiography is repeated during this period. For example, the C-arm 23 rotates at a rate of 50°/sec. With this operation, the apparatus acquires the data of a plurality of X-ray images in different radiographing directions, and stores the data in the image storage unit 3 in association with the radiographing directions (S1 and S11). For example, while the C-arm 23 rotates through 200° in four sec, the apparatus acquires X-ray images of 200 frames. The feature point designation image selection unit 7 selects key images of several frames radiographed at the same cardiac phase, e.g., end-diastolic as shown in FIG. 4, from the X-ray images of the 200 frames (S2). At the same cardiac phase, for example, a blood vessel is located at almost the same three dimensional position.

The feature point designation support unit 8 sequentially displays the key images of the several frames on the monitor 4 frame by frame in accordance with the radiographing order, and the operator designates feature points on the respective key images in accordance with the designating operation on the input device 5 (S12). This apparatus uses, as feature points, relatively identifiable markers in anatomical (morphological) terms, e.g., blood vessel branch portions, stricture portions, and stents.

The feature point designation support unit 8 supports this feature point designating operation. This support processing is a characteristic feature of this embodiment. More specifically, when a feature point is designated on the key image of the first frame (S3), the feature point designation support unit 8 determines a predictive area in which a feature point is predicted to be located on the key image of the second frame by back projection processing on the basis of the two dimensional coordinates of the feature point on the key image of the first frame and the radiographing direction of the key image of the first frame, and superimposes and displays the area on the key image of the second frame (S4). Likewise, when a feature point is designated on the key image of the second frame, the feature point designation support unit 8 determines a predictive area in which a feature point is predicted to be located on the key image of the third frame by back projection processing on the basis of the two dimensional coordinates of the feature points on the key images of the first and second frames and the radiographing directions of the key images of the first and second frames, and superimposes and displays the area on the key image of the third frame. In this manner, every time a feature point is designated, a predictive area in which a feature point is predicted to be located is displayed on the next key image.

Upon completion of designation of feature points on all the key images, the feature point three dimensional coordinate calculation unit 9 calculates the three dimensional coordinates of the feature points (S13). The apparatus then calculates the two dimensional coordinates of feature points on the remaining non-key images other than the key images, on which feature points are projected, by reprojection processing on the basis of the calculated three dimensional coordinates of the feature points and the radiographing directions of the non-key images (S5 and S14). The two dimensional coordinates of these feature points will be referred to as the calculated two dimensional coordinates of the feature points.

Subsequently, the apparatus extracts feature points from a plurality of non-key images (S6 and S15). The two dimensional coordinates of the extracted feature points will be referred to as the actual two dimensional coordinates of the feature points to discriminate them from the calculated two dimensional coordinates of the feature points. Assume that a subject image depicted on an image hardly moves between frames, and, for example, a small area of about 31×31 is set as a feature point on the image of the Nth frame. In this case, extraction processing is the processing of searching for the most morphologically similar area in the non-key image of the adjacent (N+1)th frame. Sequentially repeating this processing makes it possible to obtain the movement locus of the feature point in the initially set small area (tracking). As a similarity calculation method, this apparatus may arbitrarily use a known calculation method such as Sum of square distance, a cross-correlation method, or Mutual information.

The positional shift calculation unit 12 calculates the positional shifts of the actual two dimensional coordinates of the feature points with respect to the calculated two dimensional coordinates of the feature points as motion correction functions (S8). The positions of the non-key images are corrected on the basis of the calculated positional shifts (S8 and S16), and the data of a three dimensional image is reconstructed on the basis of the corrected non-key images and the key images (S9 and S17). The image processing unit 15 then renders the data and displays the resultant image on the monitor 4 (S18).

(Support for Feature Point Designating Operation)

Figure 6:
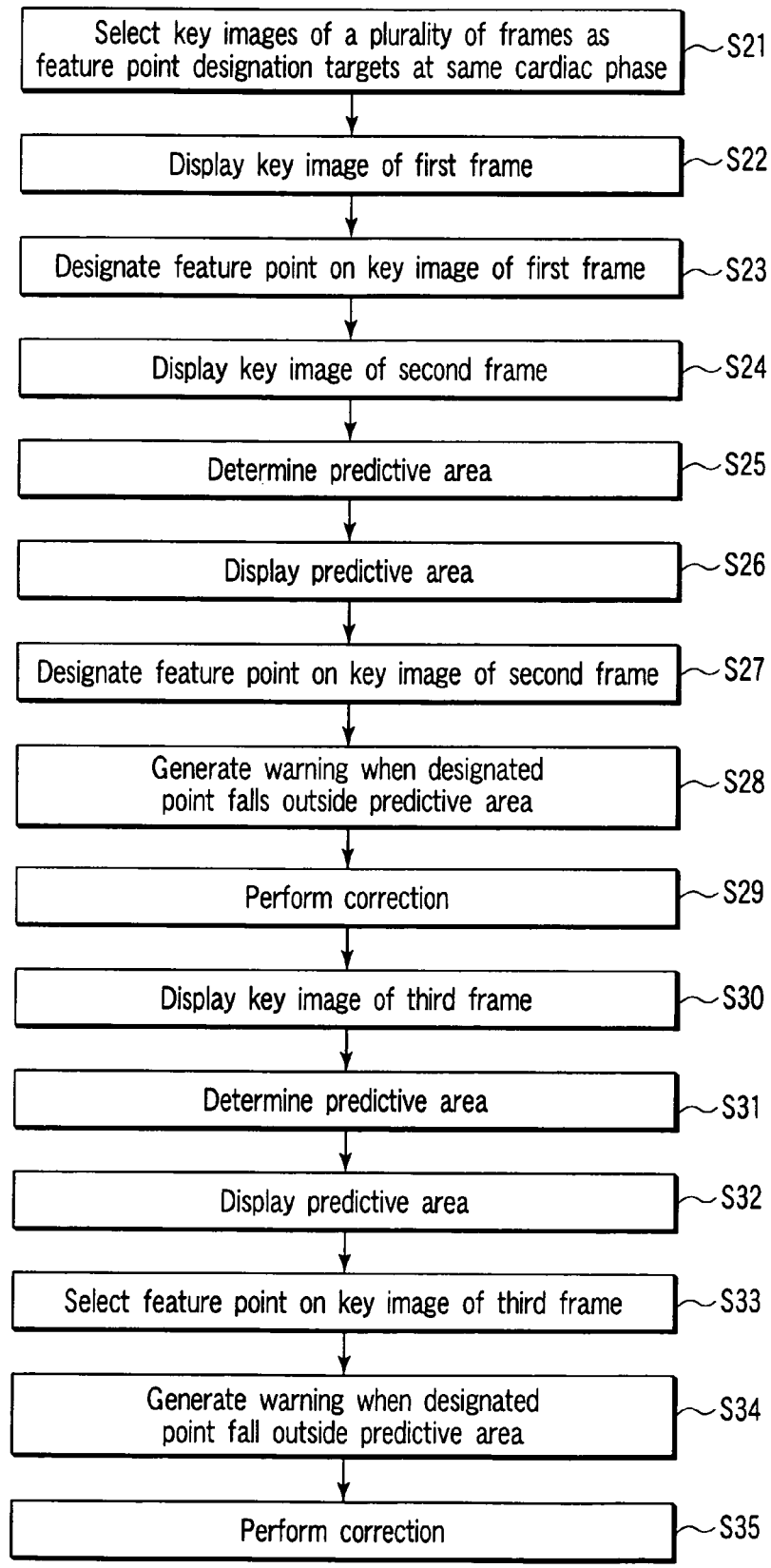
FIG. 6 is a flowchart corresponding to step S12 in FIG. 5.

Support processing for feature point designating operation by the feature point designation support unit 8 will be described below with reference to FIG. 6. When key images are selected (S21), the feature point designation support unit 8 displays the key image of the first frame on the selected images on the monitor 4 (S22). The feature point designation support unit 8 designates a feature point on the key image of the first frame in accordance with the operation of the input device 5 by the operator (S23). The feature point designation support unit 8 then displays the key image of the second frame (S24). The key image of the second frame is the image which is generated at the timing of the same cardiac phase as that at which the key image of the first frame was generated and obtained by radiography in a direction different from that of the key image of the first frame.

Figure 7:
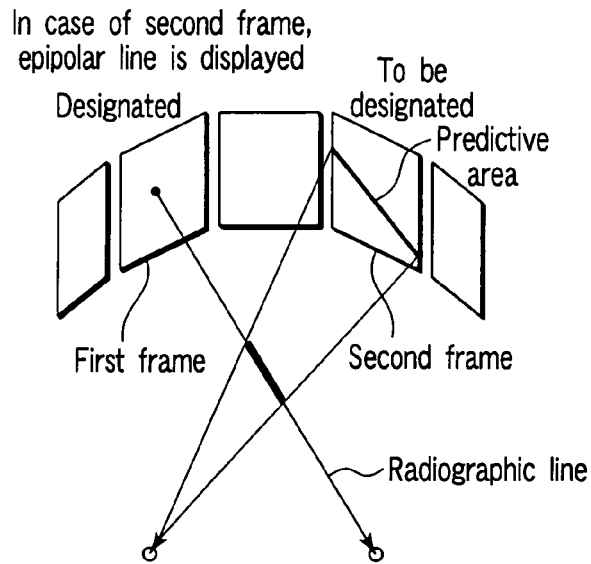
FIG. 7 is a view showing an example of display of a predictive area in step S26 in FIG. 6.
Figure 8:
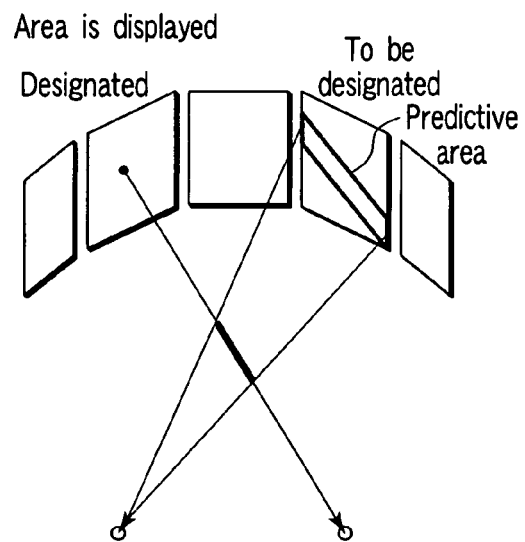
FIG. 8 is a view showing another example of display of a predictive area in step S26 in FIG. 6.

The feature point designation support unit 8 determines a predictive area in which a feature point is predicted to be located on the key image of the second frame (S25), and superimposes and displays the area on the key image of the second frame (S26). As shown in FIG. 7, the predictive area for the key image of the second frame is determined as a so-called epipolar line, drawn by projecting a projection line extending from a position corresponding to the focal point of the X-ray tube 21 to the feature point designed on the key image of the first frame, from a position corresponding to the focal point of the X-ray tube 21 at the time of radiography of the key image of the second frame to a plane corresponding to the detection surface of the X-ray detector 22. It is predicted that a feature point is located at some position on the epipolar line. Note, however, that owing to the aperiodicity of cardiac motion, a corresponding point is not necessarily located on the epipolar line. The operator searches for a feature point on the epipolar line or its periphery. As shown in FIG. 8, it suffices to enlarge the predictive area by uniformly providing a margin with a predetermined width around the epipolar line and display the resultant area as a two dimensional predictive area. This makes a feature point fall within this predictive area in most cases even with the aperiodicity of cardiac motion, thus improving supportability for feature point designation operation by the operator. The apparatus designates a feature point on the key image of the second frame in accordance with the operation of the input device 5 by the operator with the support of the predictive area (S27). If a designated point is located outside the predictive area, the feature point designation support unit 8 displays the warning message "the designated point is located outside the predictive area" on the monitor 4 (S28), and corrects the feature point on the key image of the second frame in accordance with the re-operation of the input device 5 by the operator which has received the message (S29).

Figure 9:
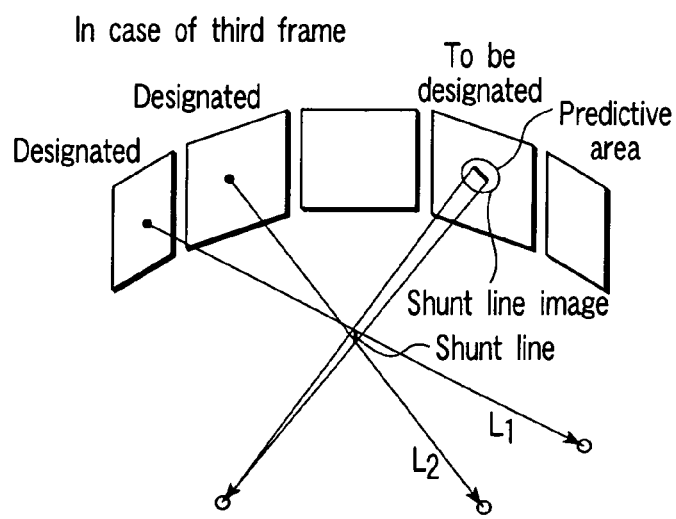
FIG. 9 is a view showing an example of display of a predictive area in step S32 in FIG. 9.
Figure 10:
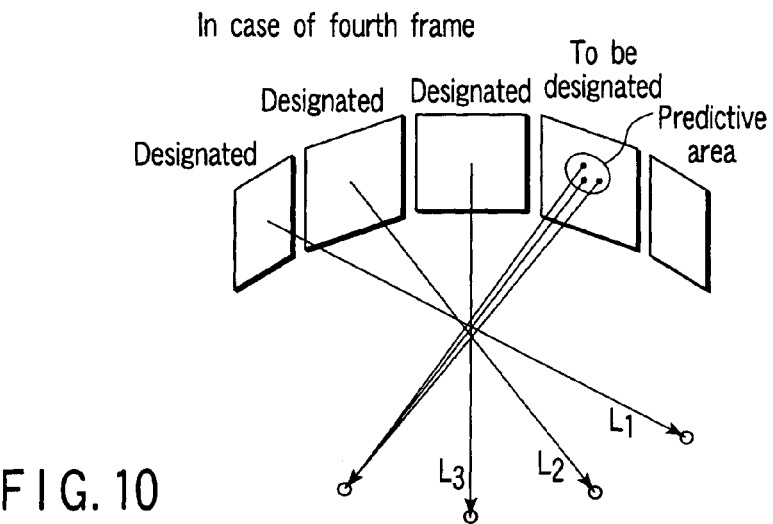
FIG. 10 is a view showing an example of display of a predictive area at the fourth or subsequent frame in this embodiment.

The feature point designation support unit 8 then displays the key image of the third frame (S30), and determines a predictive area to be displayed on the key image of the third frame (S31). Assume that the operator has already designated feature points on the key images of the first and second frames and tries to designate a feature point on the key image of the third frame. In this case, as shown in FIG. 9, since projection lines L1 and L2 extending to the already designated feature points can be drawn, it can be estimated that the three dimensional position of a feature point is the intersection point between the projection lines L1 and L2. Projecting this intersection point on the key image of third frame can set predictive coordinates. In practice, however, owing to the aperiodicity of cardiac motion, the projection lines L1 and L2 do not often intersect. For this reason, the shortest straight line (shunt line) which connect the projection lines L1 and L2 is specified, and the shunt line is projected on the key image of the third frame. As in the case shown in FIG. 8, the feature point designation support unit 8 specifies, as a predictive area, the elliptic area obtained by providing a margin around the projected shunt line image (S31), and superimposes and displays the area on the key image of the third frame (S32). The apparatus designates a feature point on the key image of the third frame in accordance with the operation of the input device 5 by the operator with the support of the predictive area (S33). If a designated point is located outside the predictive area, the feature point designation support unit 8 displays the warning message "the designated point is located outside the predictive area" on the monitor 4 (S34), and corrects the feature point on the key image of the third frame in accordance with the re-operation of the input device 5 by the operator which has received the message (S35).

Figure 11:
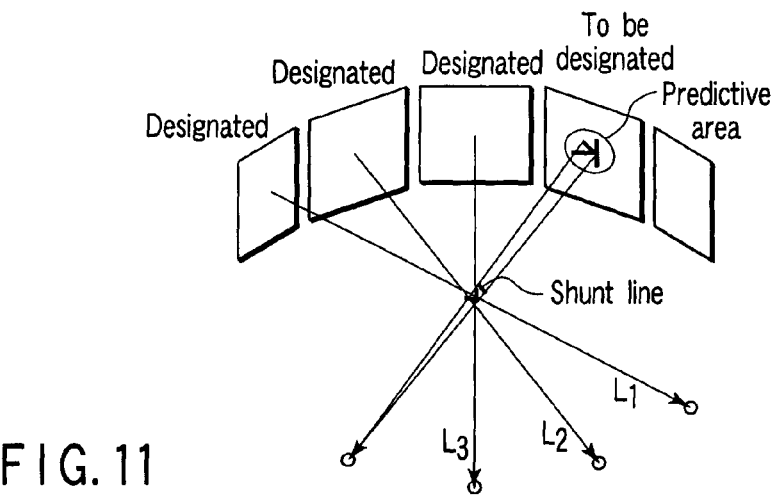
FIG. 11 is a view showing another example of display of a predictive area at the fourth or subsequent frame in this embodiment.

In the case of the fourth or subsequent frame, as shown in FIG. 11, many projection lines such as projection lines L1, L2, and L3 can be drawn, and the intersection point between them can be estimated as the three dimensional position of the feature point. Owing to the aperiodicity of cardiac motion, however, the projection lines L1, L2, and L3 do not intersect. For this reason, the feature point designation support unit 8 projects the midpoint of the shunt line between the projection lines L1 and L2, the midpoint of the shunt line between the projection lines L2 and L3, and the midpoint of the shunt line between the projection lines L1 and L3 onto the key image of the fourth frame. The feature point designation support unit 8 then obtains the barycenter of the three projected points, and determines, as a predictive area, the circular or elliptic area obtained by providing a margin around the barycenter so as to contain all the three points.

Figure 12:
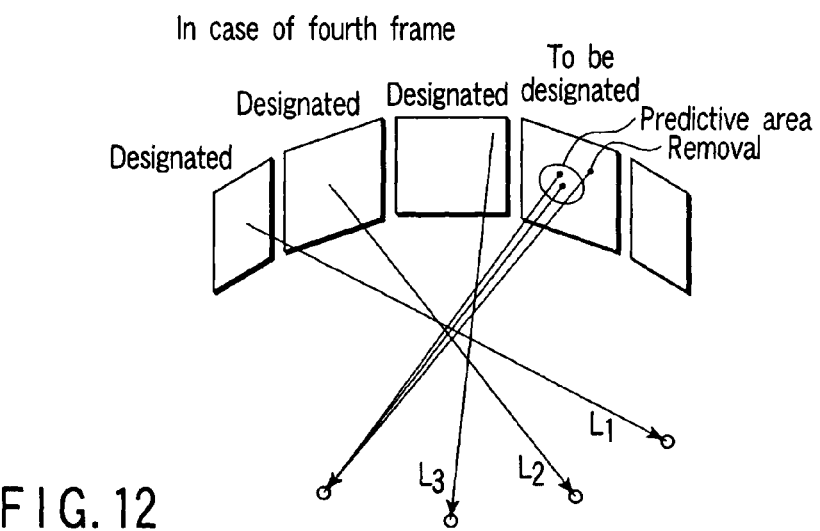
FIG. 12 is a view showing another example of display of another predictive area at the fourth or subsequent frame in this embodiment.

As another technique of determining a predictive area for the fourth or subsequent frame, there is available a technique of projecting the shunt line between the projection lines L1 and L2, the shunt line between the projection lines L2 and L3, and the shunt line between the projection lines L1 and L3 onto the key image of the fourth frame, as shown in FIG. 12. The feature point designation support unit 8 then obtains the barycenter of the three projected shunt line images and determines, as a predictive area, the circular or elliptic area obtained by providing a margin around the barycenter so as to contain all the three lines.

Assume that at the fifth or subsequent frame, as shown in FIG. 12, the aperiodicity of cardiac motion is very noticeable as in a case wherein the cardiac motion is arrhythmia. In this case, the feature point designation support unit 8 obtains the coordinates of the barycenter between the midpoint of the shunt line between the projection lines L1 and L2, the midpoint of the shunt line between the projection lines L2 and L3, and the midpoint of the shunt line between the projection lines L1 and L3, and also obtains a variance σ. If a given midpoint falls within a distance of 3σ from the barycenter, the feature point designation support unit 8 regards this point as a normal point. If a given midpoint falls outside a distance of 3σ from the barycenter, the feature point designation support unit 8 regards this point as an abnormal point and excludes it. After the exclusion, the feature point designation support unit 8 calculates the barycenter between the remaining midpoints and checks exclusion again. If all midpoints become normal points, the feature point designation support unit 8 determines the points as the estimated three dimensional coordinates of the feature point.

Although the above description has exemplified the numerical values which are expected to be used most frequently, the numerical values described above are examples, and the present invention is not limited to them. For example, the size of a margin can be arbitrarily set, a predictive area may have a circular shape, a rectangular shape, or an arbitrary shape instead of an elliptic shape, and a barycenter need not be the barycenter but may be an average (median). In addition, the distance may be 3σ or 2σ, and the present invention may use an index other than the variance σ.

Figure 13:
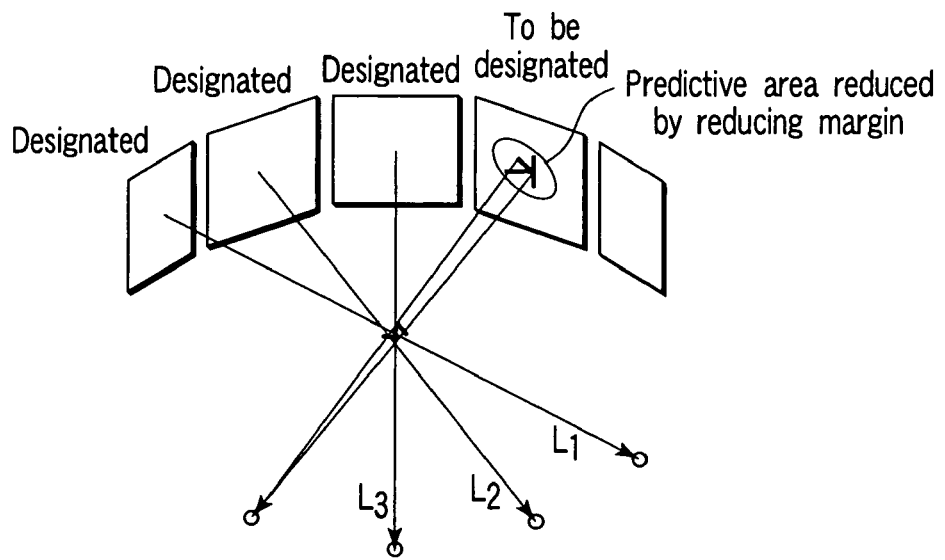
FIG. 13 is a view showing an example of display of a reduced predictive area in this embodiment.
Figure 14:
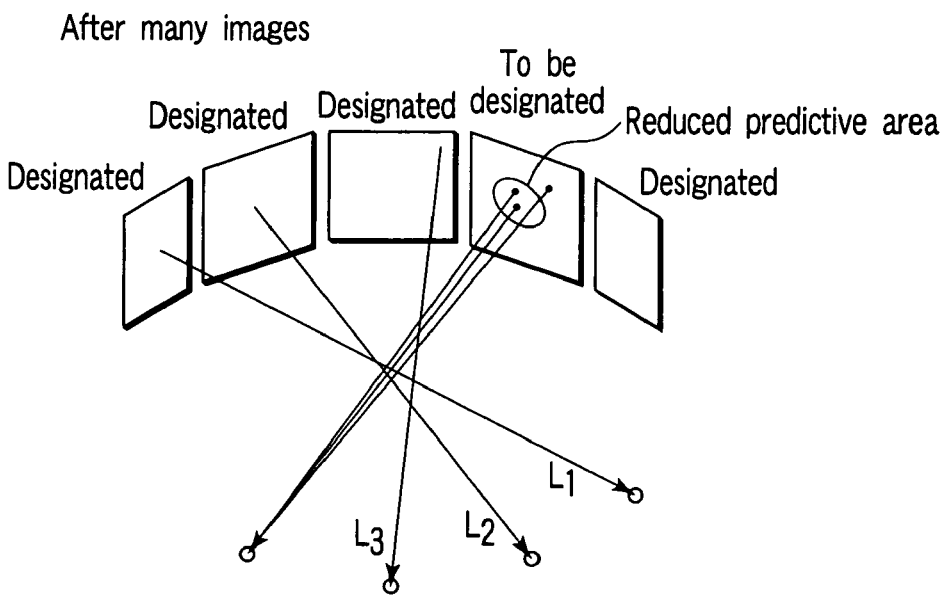
FIG. 14 is a view showing an example of display of a reduced predictive area in this embodiment.

As the number of designated frames increases to six or more, it can be thought that the reliability of a range in which projection lines intersect increases. In this case, as shown in FIGS. 13 and 14, since the accuracy of an ellipse to be displayed gradually improves, the margin may be decreased as the number of frames increases.

Figure 15:
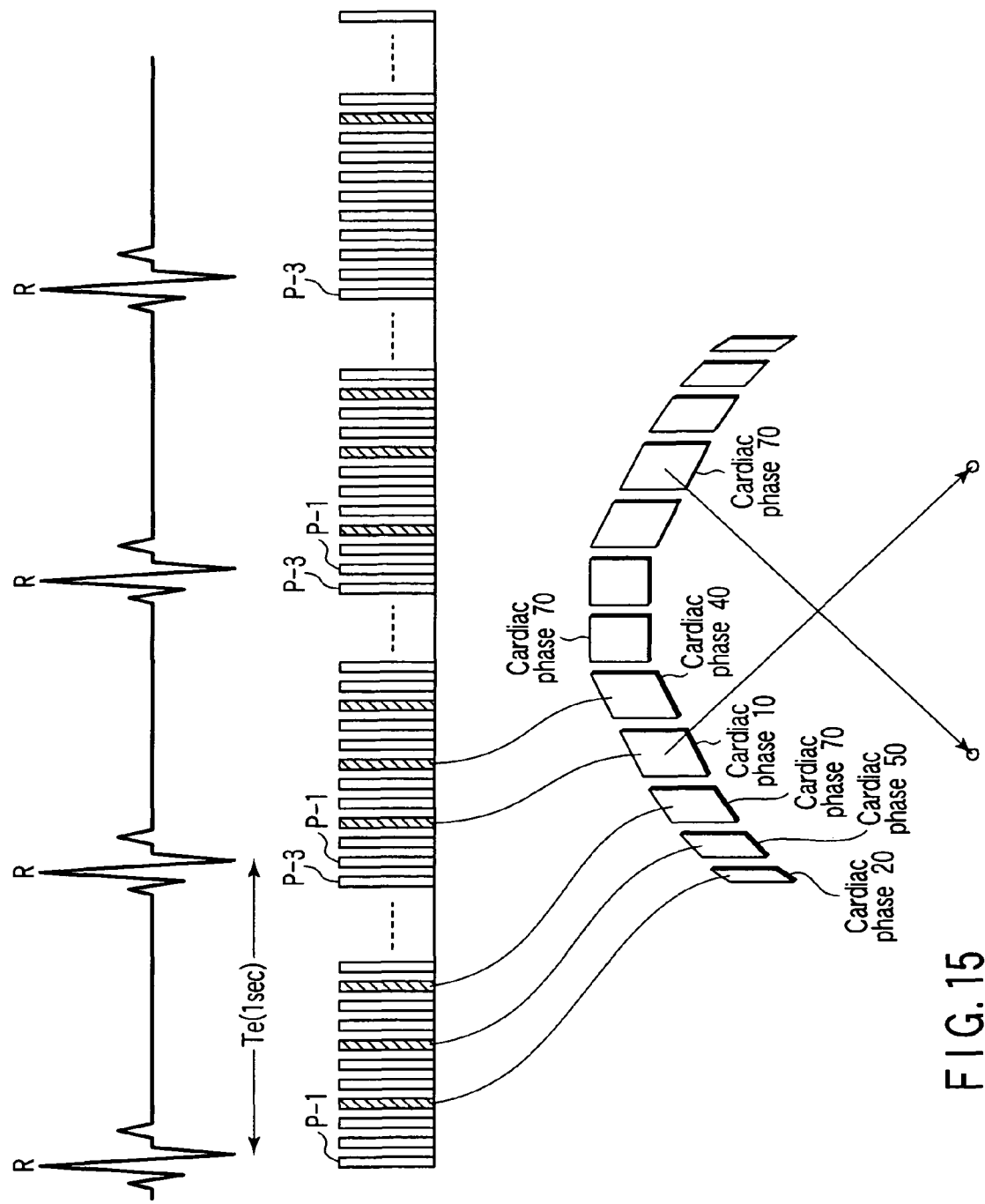
FIG. 15 is a view showing another example of a selected image (key frame) selection method in step S2 in FIG. 3.

According to the above description, images at the same cardiac phase are selected as key images. However, as shown in FIG. 15, it suffices to select, as key images, images at different cardiac phases which the operator arbitrarily designates.

Figure 16:
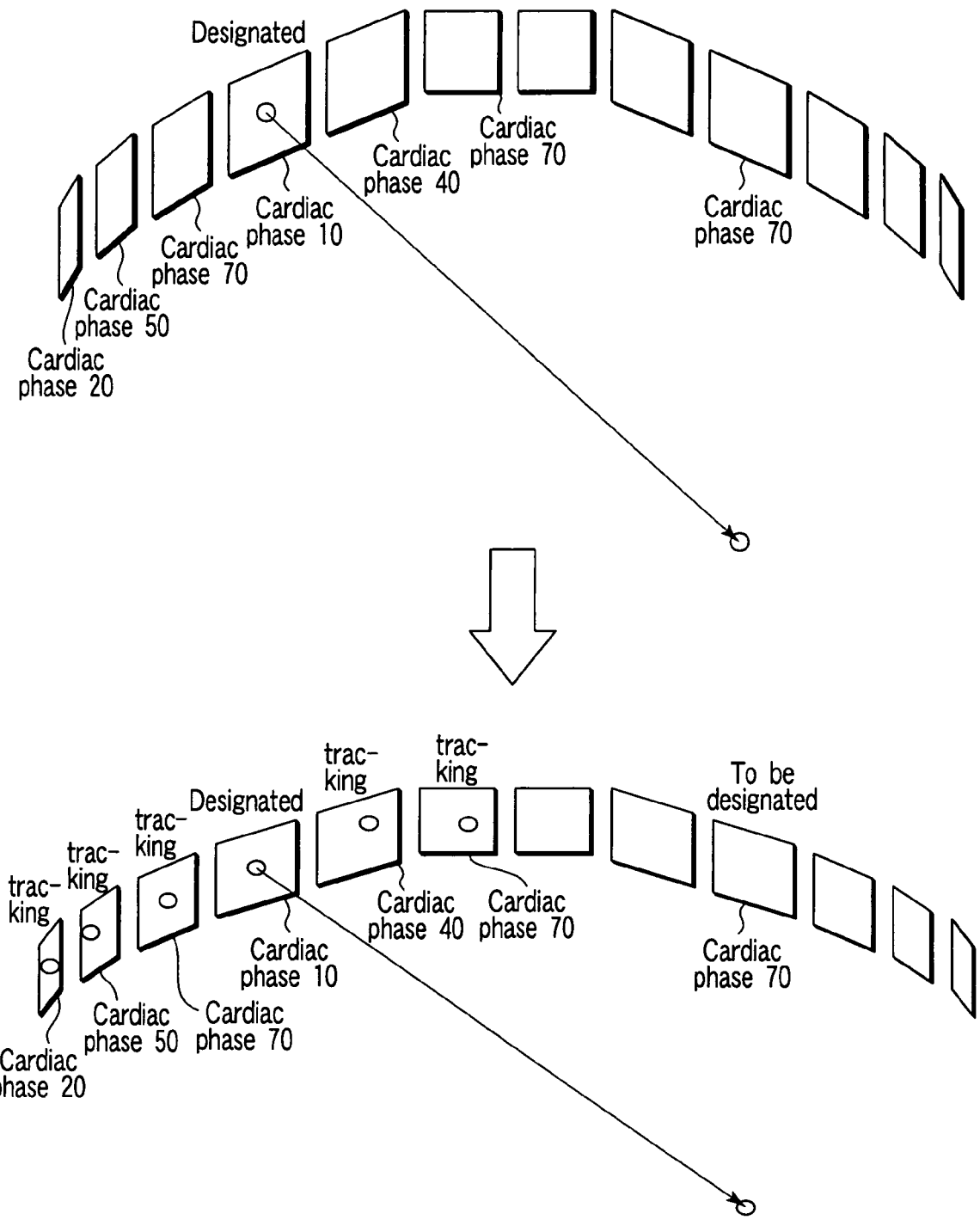
FIG. 16 a supplementary view for explaining a procedure of placing tracking step S15 immediately after feature point designation step S12 in FIG. 5.

According to the above description, the apparatus executes tracking processing for non-key images upon completion of designation of feature points on all key images. As shown in FIG. 16, however, it suffices to execute tracking of feature points with respect to non-key images after a feature point is designated on the key image of a given frame before a feature point is designated on the key image of the next frame. In the case shown in FIG. 16, the operator designates a feature point on a frame at cardiac phase 10, and the apparatus executes tracking processing for feature points with respect to non-key images within a projection direction range of 30° centered on an image spatially near the feature point, e.g., a key image. Since a larger tracking error occurs at a remoter frame, the operator is required to designate a feature point. In this case, for example, the operator designates a feature point at a frame at a cardiac phase of 70%. According to the method described above, when a feature point is to be designated at a frame at cardiac phase 70, a feature point is obtained from other frames at cardiac phase 70 on which feature points have already been designated. In this case, the apparatus sets, as the next feature point designation target, another frame at the same cardiac phase as cardiac phase 70 at which feature point designation has not been performed but tracking has been performed. If there are two or more other frames at cardiac phase 70 at which tracking has been performed, a predictive area can be estimated by the same technique as that described above.

Not that the above feature point designation support mode can be turned on/off in accordance with an instruction from the operator. Alternatively, when the operator presses the "assist" button, the apparatus may display a predictive area.

According to the processing algorithm to be implemented in the end, "the three dimensional coordinates of a feature point are obtained and projected on a key image". For this purpose, it is necessary to obtain feature point coordinates on a plurality of key images from at least two directions. In addition, a plurality of key images correspond to the same cardiac phase. For this reason, this apparatus acquires electrocardiogram signals (ECG) while acquiring images, and selects images at the cardiac phase by referring to electrocardiographic waveforms. More specifically, assume that 200 images are obtained from, for example, the 200° direction, and five heartbeats have occurred as cardiac motion during this period. In this case, since there are five frames at the same cardiac phase, it suffices to select any two of the five frames. Considering actual cardiac motion, although the heart moves periodically, cardiac motion is not periodic motion in a strict sense. Therefore, when two frames are arbitrarily selected from five frames and projection lines are drawn in a three dimensional space, the projection lines hardly intersect. If they slightly shift even though they do not intersect, it may suffice to define the midpoints of the projection lines. However, when, for example, arrhythmia occurs in some patients, projection lines greatly shift from each other. In this case, defining midpoints will lead to wrong calculated three dimensional coordinates. This will deform the shape of a final three dimensional image.

Figure 18:
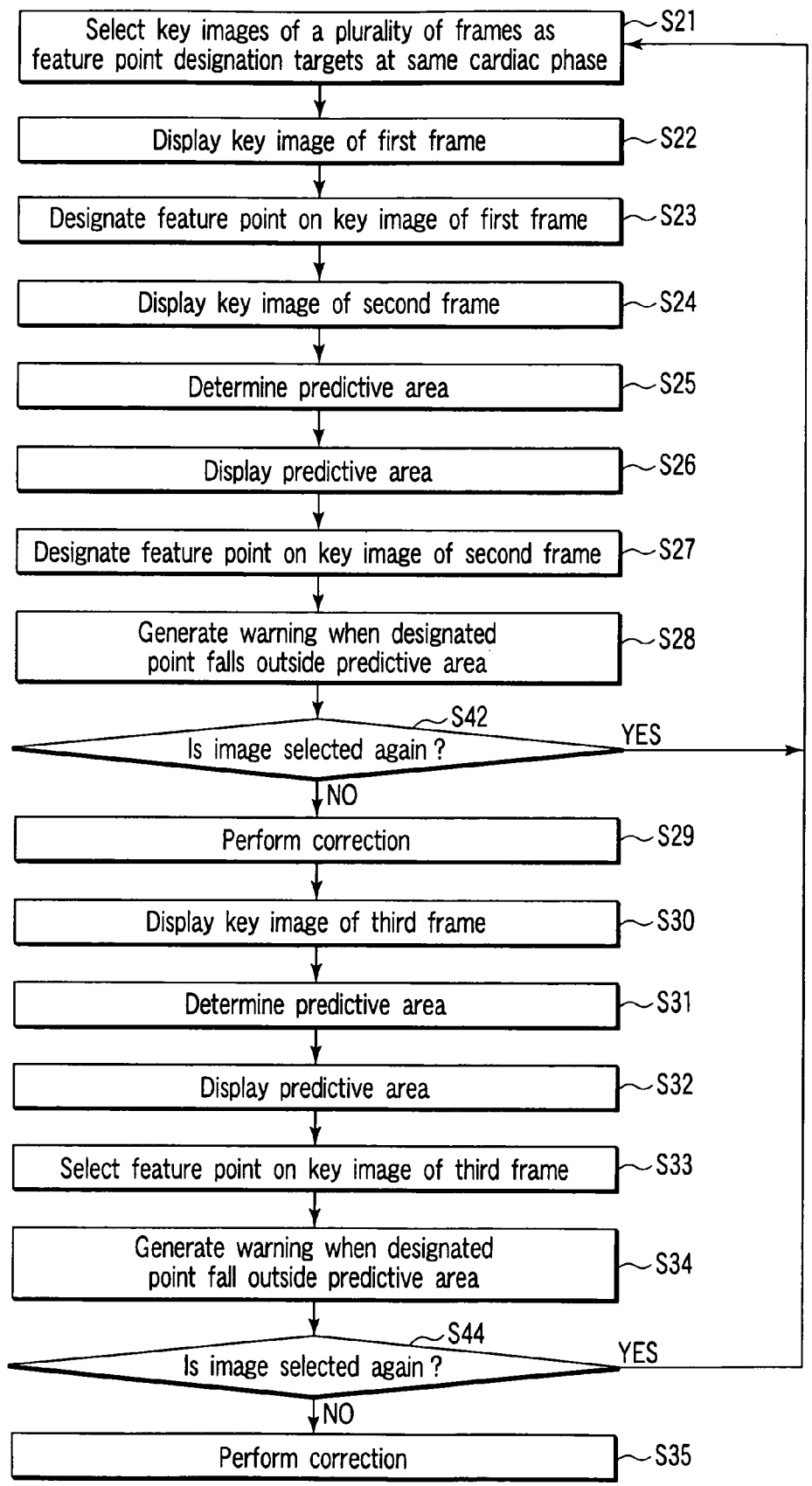
FIG. 18 is a view showing a modification of FIG. 6.

As shown in FIG. 18, when the operator designates a feature point on the second or subsequent frame, the feature point designation support unit 8 extracts the maximum distance from the shunt lines between a plurality of projection lines L, and compares the maximum distance with a threshold. If the maximum distance exceeds the threshold, the apparatus displays a message for prompting the operator to select a key image again (S42 and S44). More specifically, the "key image reselection" button is placed on a GUI and is changed to a designatable state.

Figure 19:
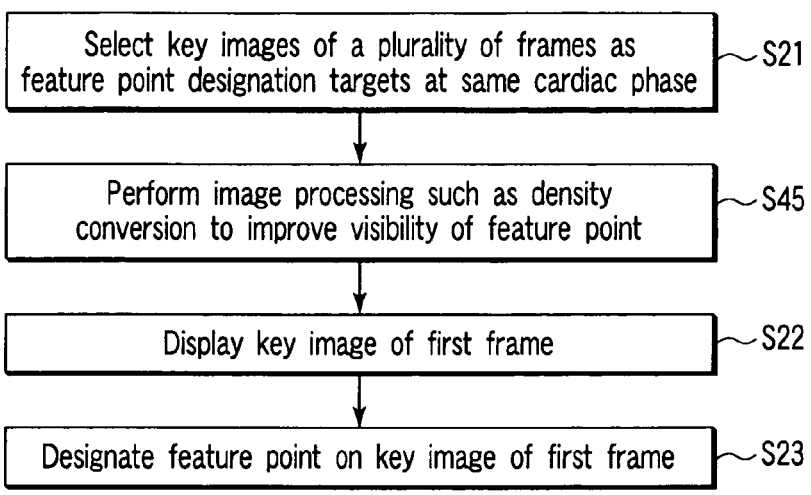
FIG. 19 is a view showing a modification of FIG. 6.
Figure 20:
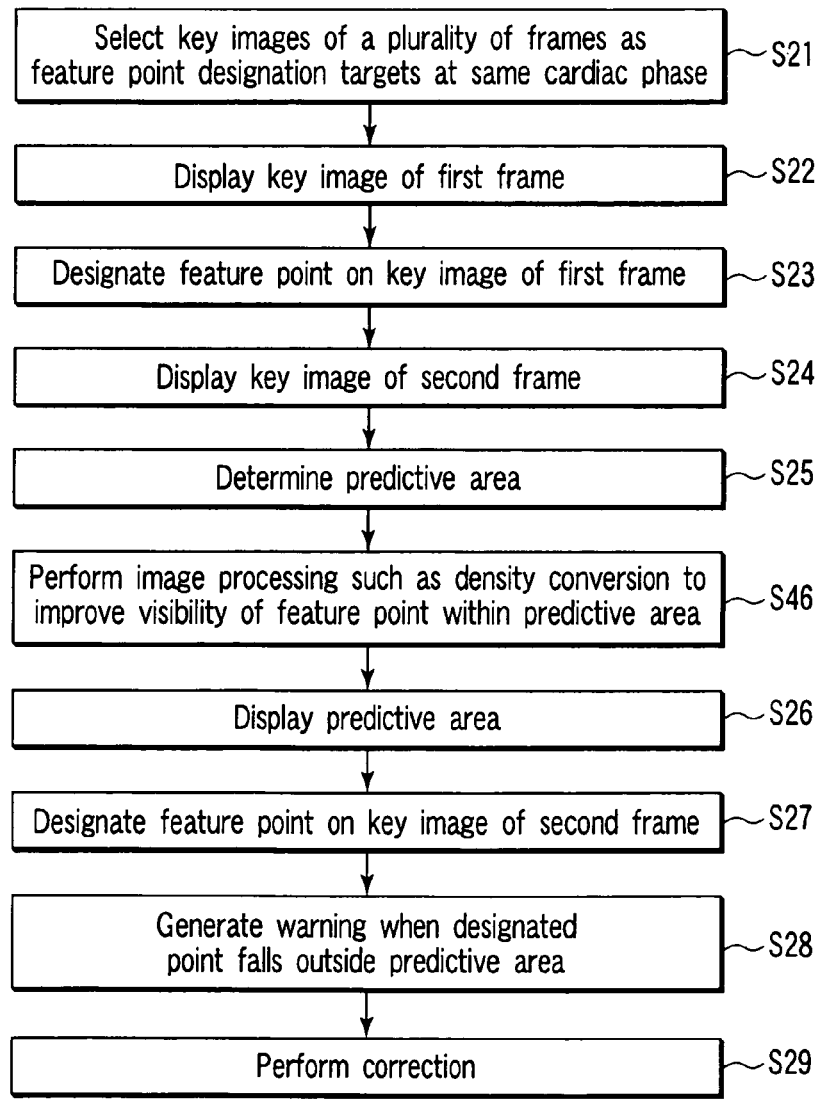
FIG. 20 is a view showing a modification of FIG. 6.

In addition, this apparatus displays a key image and a predictive area together to designate a feature point. When, however, a key image is displayed as an acquired image, a feature point portion may be completely blackened or whitened depending on X-ray conditions and subject conditions, resulting in difficult discrimination. For this reason, instead of displaying an acquired image as a key image without any change, the apparatus displays, as a key image, the image obtained by performing image processing (preprocessing) such as density conversion using the image processing unit 15 to improve the visibility of a feature point, as shown in FIG. 19. As image processing, it suffices to select and combine general kinds of image processing such as gamma correction, density compression, histogram flattening, and high-pass filter processing. In addition, as shown in FIG. 20, when a predictive area is set, the apparatus performs optimal image processing within the predictive area and displays the resultant image. This further improves the visibility of the predictive area as compared with the case wherein the overall density of the image is optimized.

Figure 21:
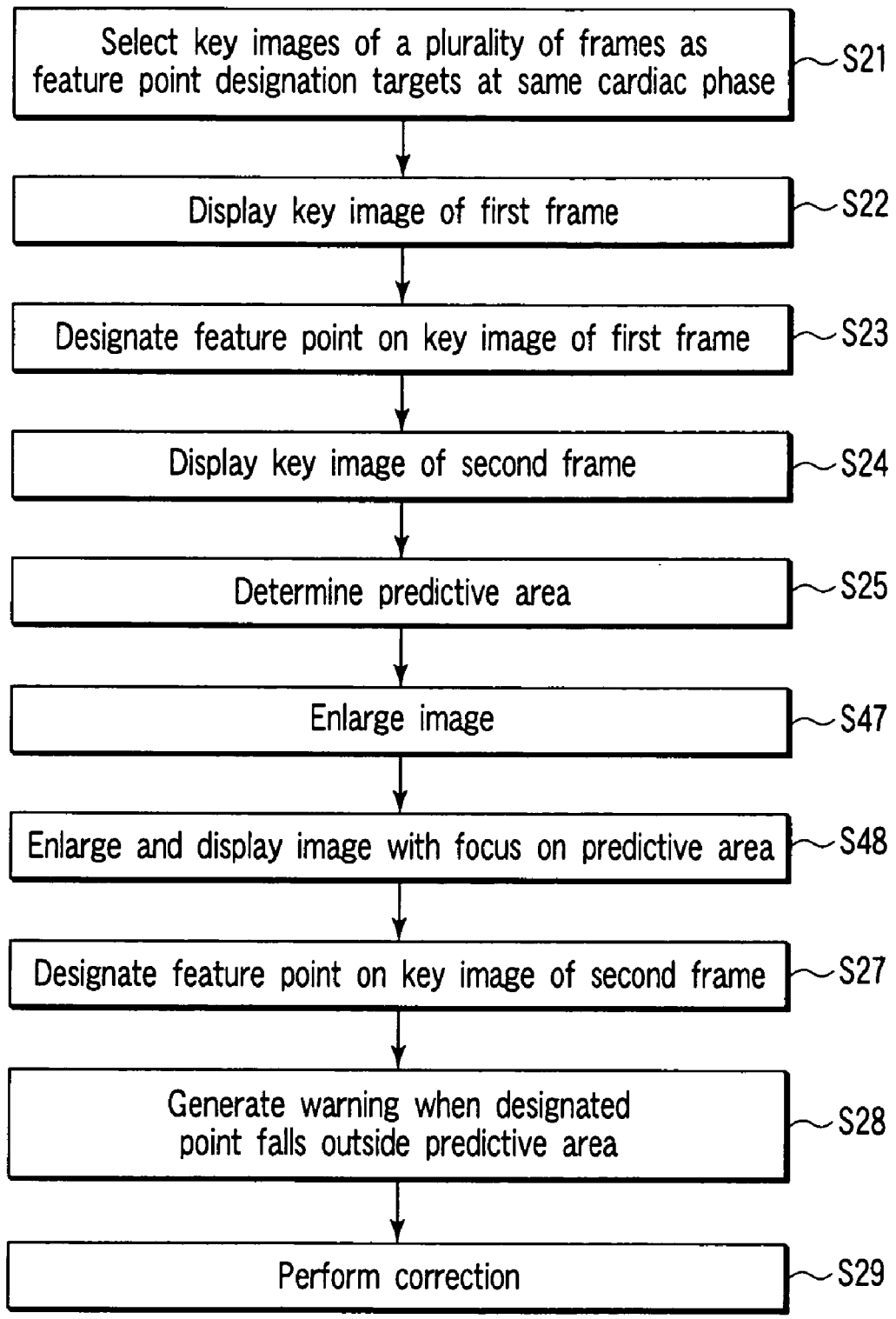
FIG. 21 is a view showing a modification of FIG. 6.
Figure 22:
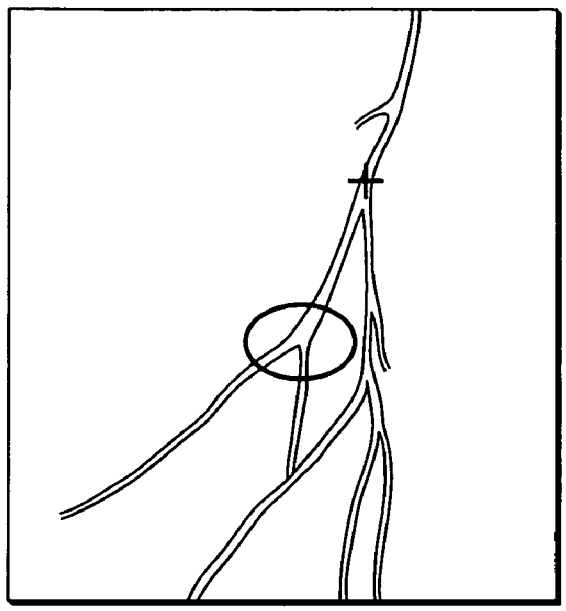
FIG. 22 is a supplementary view for explaining steps S47 and S48 in FIG. 21.
Figure 23:
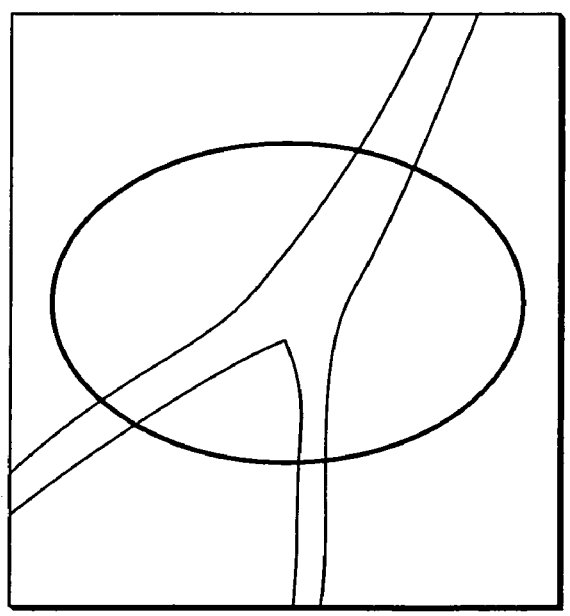
FIG. 23 is a supplementary view for explaining steps S47 and S48 in FIG. 21.

Although this apparatus displays a key image together with a predictive area to designate a feature point, when the key image is displayed as the acquired image without any change, the predictive area is small as compared with the entire image and may be difficult to discriminate (FIG. 22). As shown in FIG. 21, therefore, the image processing unit 15 enlarges the key image (S47), and the apparatus displays the enlarged key image on the monitor 4 with a focus on the predictive area (FIG. 23). This allows the operator to easily discriminate the predictive area and click the mouse.

As image processing, this apparatus may modulate the densities of a plurality of keys to make their average luminances become almost equal. This embodiment is typically applied to rotational radiography of the heart. The place where the heart is located greatly changes in body thickness. For this reason, acquired images greatly vary in image luminance for each frame. More specifically, an image radiographed from the front is bright because the body thickness is small. An image radiographed from a side is dark because the body thickness is large. In order to make these luminances as uniform as possible, luminance modulation is applied to key images to make their average luminances equal. Luminance does not abruptly changes between frames but gradually changes from the front to the side.

As image processing, background removal processing is effective. A three dimensional reconstruction target is typically a heart blood vessel, and hence the lung field, bones, and the like are not necessary. Processing for emphasizing a heart blood vessel is effective. More specifically, this apparatus preferably performs band-pass filtering processing or Morphology filtering processing to decrease the contrast of a portion other than the size of a heart blood vessel. In addition, since a heart blood vessel is dynamic, the processing of removing a still portion is effective. More specifically, the apparatus generates a three dimensional image associated with a subject other than coronary vessels by reconstruction processing without any motion correction of a plurality of X-ray images, generates a projection image by performing projection processing for the three dimensional image with respect to the radiographing direction, and calculates the difference between the projection image and the original X-ray image.

In addition, after the operator designates a feature point on the key image of the first frame, the apparatus tracks a feature point on the next key image, sets a region of interest (ROI) with a predetermined size centered on the tracked point, and perform density modulation processing to optimize the contrast of a heart blood vessel within the ROI.

Furthermore, this apparatus requires the key images of at least two frames. In consideration of accuracy, in practice, the apparatus uses five to 10 frames. As the number of frames of key images increases, the operator may forget how he/she designated feature points on frames in the past, and hence may want to refer to the past frames. The following shows various examples of display.

As shown in FIGS. 24A, 24B, and 24C, when displaying the key images of the second and subsequent frames on the monitor 4, the feature point designation support unit 8 displays, side by side, frames on which feature points were designated in the past. As shown in FIGS. 25A, 25B, and 25C, when displaying the key images of the second and subsequent frames on the monitor 4, the feature point designation support unit 8 displays, side by side, frames on which feature points have been designated immediately before the key images. As shown in FIGS. 26A, 26B, and 26C, when displaying the key images of the second and subsequent frames on the monitor 4, the feature point designation support unit 8 displays the key images of two frames on which feature points have been designated on the left and right sides of the key image in the feature point designation step. As shown in FIGS. 27A, 27B, and 27C, when displaying the key images of the second and subsequent frames on the monitor 4, the feature point designation support unit 8 displays the key image in the feature point designation step in a large size while displaying the key images on which feature points have been designated in thumbnails. As shown in FIGS. 28A, 28B, and 28C, when displaying the key images of the second and subsequent frames on the monitor 4, the feature point designation support unit 8 displays the entire key image in the feature point designation step while displaying portions of the key images on which feature points have been designated with a focus on the feature point of each image. In addition, as shown in FIG. 28D, it suffices to arrange a designation target image and preceding and succeeding images in an arcuated form. Furthermore, as shown in FIG. 28E, it suffices to display a designation target image located in the middle in a size larger than those of preceding and succeeding images.

Figure 29:
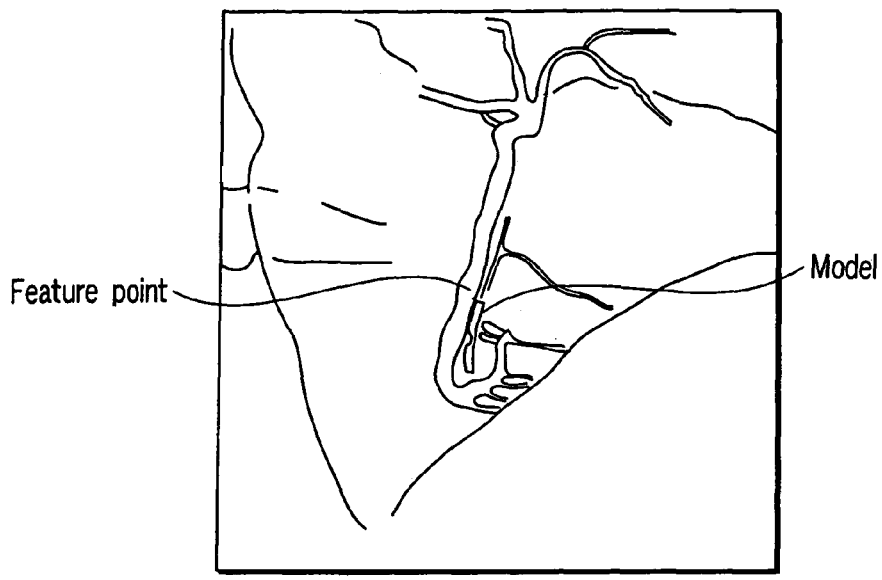
FIG. 29 is a view showing a blood vessel model superimposed and displayed on an image in this embodiment.

According to the above description, the apparatus determines a predictive area such as an epipolar line and superimposes and displays it on a key image. The apparatus may generate a blood vessel center line by using the support unit 8 and superimpose and display it on a key image instead of or together with a predictive area. According to a processing method for this operation, blood vessel center lines are manually acquired on two or more key images at the same cardiac phase or automatically acquired by area extraction. The apparatus then calculates the three dimensional coordinates of the blood vessel center lines from the two dimensional coordinates of the blood vessel center lines, and projects them on the frame of another key image, thereby generating an image. When displaying this image, the apparatus preferably displays the blood vessel center line of the main blood vessel and the blood vessel center lines of the branch blood vessels in different colors. In addition, as shown in FIG. 29, the feature point designation support unit 8 may generate and display a blood vessel model by obtaining the diameter (width) of the blood vessel at each position on the blood vessel center line on one of the key images.

(Feature Point Tracking)

Figure 30:
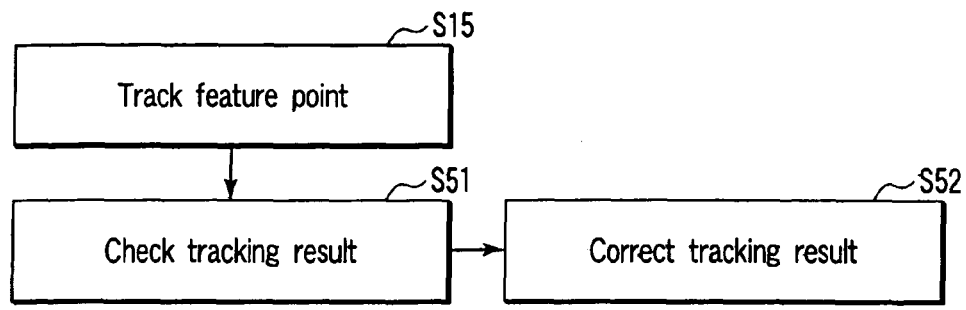
FIG. 30 is a view showing correction processing for a tracking result in step S15 in FIG. 5.

As shown in FIG. 30, the feature point extraction (tracking) unit 11 displays the tracking result in step S15 described above on the monitor 4 to allow the operator to check the result (S51). That is, the operator visually checks the tracking result output from the feature point extraction unit 11. If the tracking result is proper, the operator presses the OK button. The process then immediately advances to step S16. If the tracking result is not proper, the operator presses the NG button, and manually corrects the position of the feature point (S52). This makes it possible to suppress a deterioration in image quality due to a tracking error.

Figure 31:
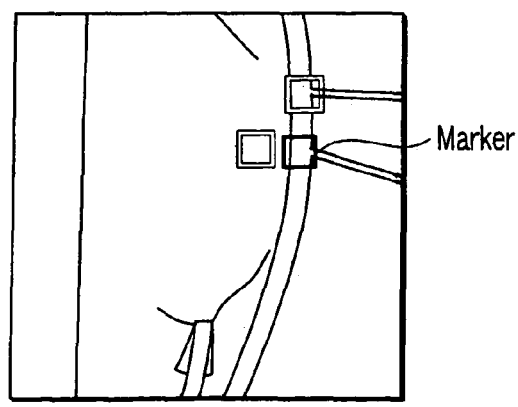
FIG. 31 is a view showing an example of display of the tracking result in step S51 in FIG. 30.
Figure 32:
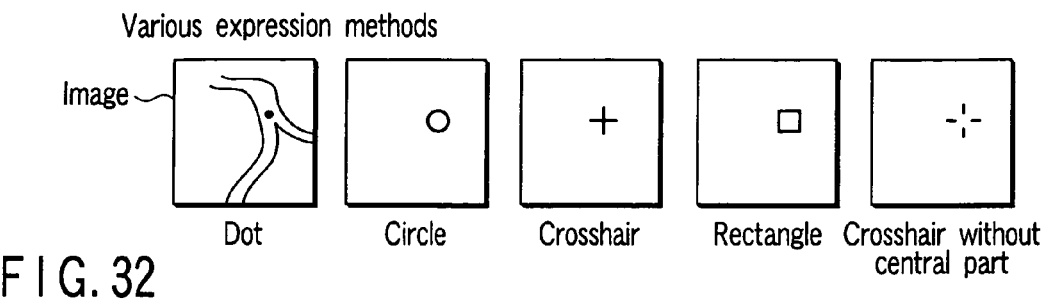
FIG. 32 is a view showing an example of a marker of the tracking result in step S51 in FIG. 30.
Figure 33:
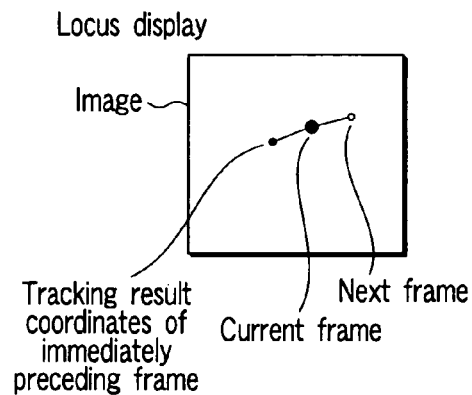
FIG. 33 is a view showing an example of display of the locus of the tracking result in step S51 in FIG. 30.
Figure 46:
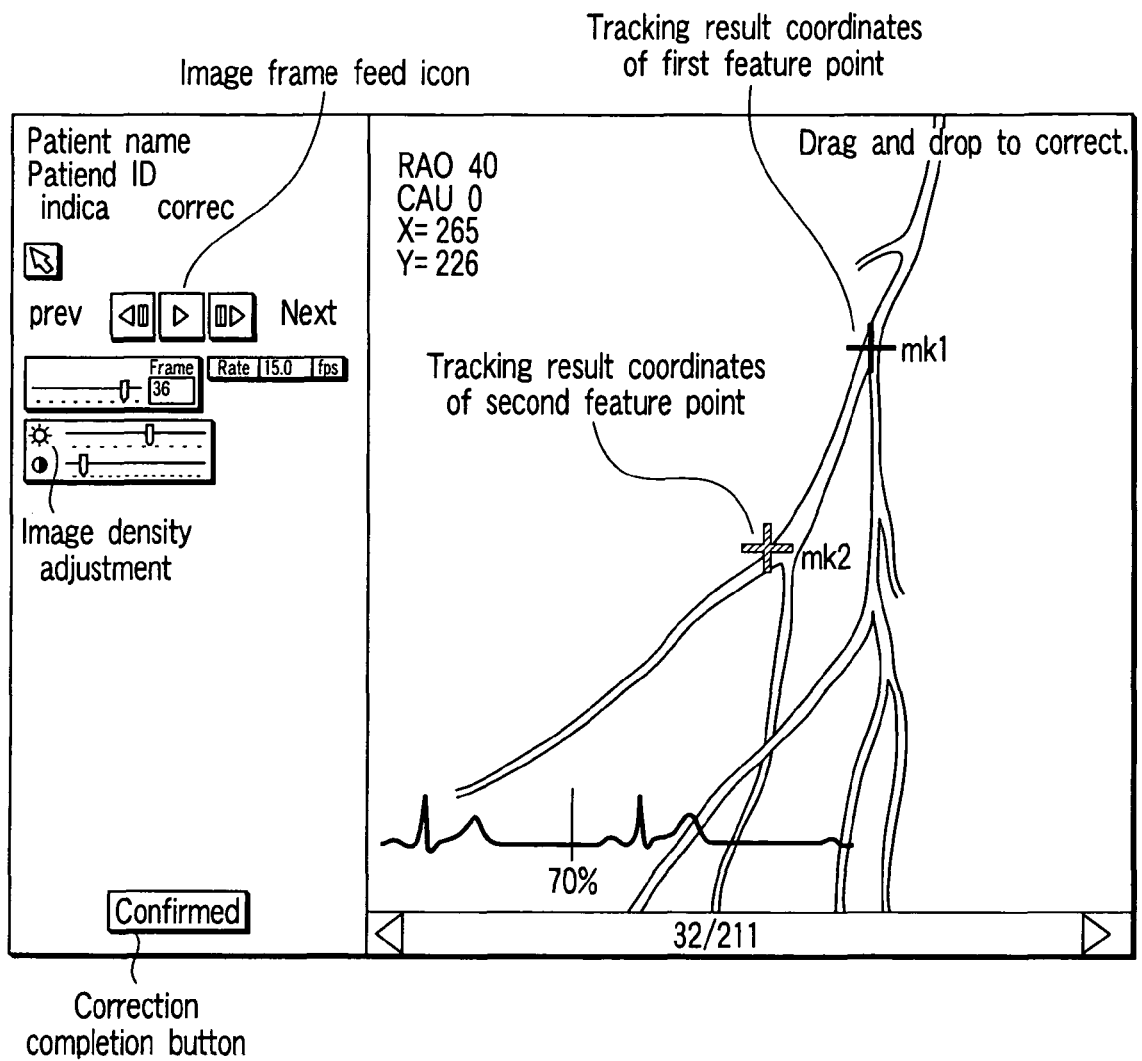
FIG. 46 is a view showing a concrete display example of the tracking result in FIG. 30.

Upon completion of the tracking processing, the feature point extraction unit 11 superimposes and displays a marker indicating the tracked feature point on an unselected image (overlay display), as exemplified in FIGS. 31 and 46. The marker is displayed in monochrome or color. The marker is typically a dot, a circle, a crosshair, a rectangle, or a crosshair without the central part, as shown in FIG. 32. Note that the rectangular marker has a size equal to that of a template used for tracking. Alternatively, as shown in FIG. 33, the apparatus may superimpose and display a marker indicating a tracked feature point on a current unselected image together with a marker indicating a feature point tracked from an immediately preceding unselected image and a marker indicating a feature point tracked from the next unselected image. The apparatus may also connect these markers with a line and display the resultant image as a locus representing the movement of a feature point.

Note that there are target images of about 200 frames, which are displayed as a moving image. With respect to the image of one frame in the moving image, a tracking result on the frame is displayed. This apparatus allows an interface on which a moving image is displayed to perform single frame playback, slow playback, and reverse playback. This interface has icons or a keyboard function for operation. When a plurality of feature points are designated at a plurality of regions in an image and tracking is concurrently performed with respect to a plurality of feature points, the apparatus displays a plurality of tracking results. The apparatus displays the plurality of tracking results in different colors, shapes, thicknesses, with different numbers, and the like. When tracking a plurality of feature points, the apparatus can independently display them one by one. In addition, the apparatus includes an interface with an icon or menu which allows independent display.

The apparatus displays tracking results on unselected images (about 100 to 200 frames) as tracking targets and tracking results on selected images (about 2 to 10 frames) as feature point designation targets in different colors, e.g., displays the former results in red and the latter results in black, so as to discriminate them. The image processing unit 15 can perform window processing, gamma adjustment, and enlargement/reduction with respect to display images.

Figure 34:
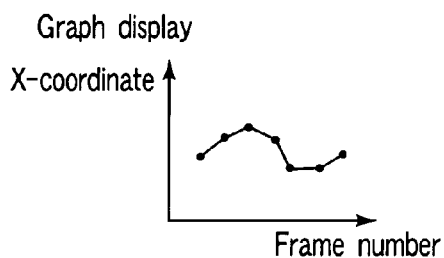
FIG. 34 is a view showing an example of display of a graph representing the tracking result in step S51 in FIG. 30.
Figure 35:
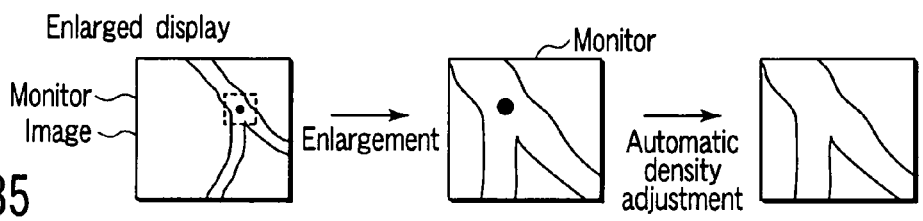
FIG. 35 is a view showing an example of display of an enlarged view of the tracking result in step S51 in FIG. 30.

As shown in FIG. 34, for example, the feature point tracking unit 11 can display, as a tracking result, a change in a coordinate of a tracked feature point, e.g., the X-coordinate, in the form of a graph. As shown in FIG. 35, the feature point extraction unit 11 can make the image processing unit 15 enlarge an image to enlarge/display a tracked feature point with a focus on the coordinates of the point. This can facilitate correcting operation by enlarging an image. That is, displaying an image in a too small size makes it difficult to correct the position of a feature point. Displaying only an image makes it impossible for the operator to determine which part of the image is to be enlarged. Displaying tracking result coordinates allows the operator to know that he/she should enlarge and display the corresponding portion. In addition, as shown in FIG. 35, the feature point extraction unit 11 may make the image processing unit 15 adjust the overall density of an image on the basis of a density near a feature point. Automatically adjusting a density from the overall density information of an image does not always optimize the density near tracking coordinates. Optimizing the density from data near the tracking coordinates allows the operator to easily see a portion near the tracking coordinates and correct it.

Figure 36:
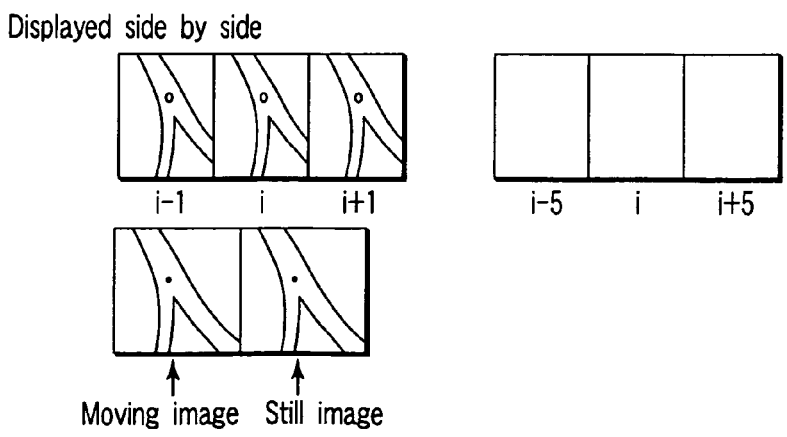
FIG. 36 is a view showing an example of displaying a plurality of tracking results side by side in step S51 in FIG. 30.

Display images can be displayed one by one or can be displayed side by side (tiled). As shown in FIG. 36, this apparatus simultaneously displays the images of three frames. The apparatus places an image of interest in the middle of images, and displays the preceding and succeeding frames on the left and right sides of the image of interest. Alternatively, the apparatus places an image of interest in the middle of images, and displays, for example, the image five frames preceding the image of interest and the image five frame succeeding the image of interest on the left and right sides of the image of interest. Alternatively, the apparatus places an image of interest in the middle of images, and displays two images arbitrarily designated by the operator on the left and right sides of the image of interest. Alternatively, the apparatus displays an image of interest as a still image, and displays the X-ray images of a total of 200 frames as rotating moving images on one side of the image of interest.

Figure 37:
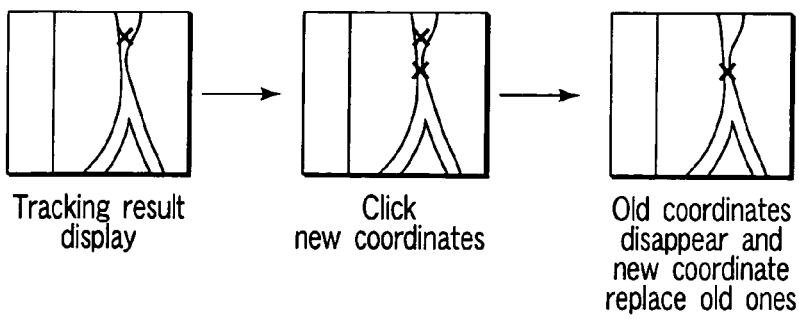
FIG. 37 is a view showing a procedure of correcting a tracking result in step S52 in FIG. 30.
Figure 38:
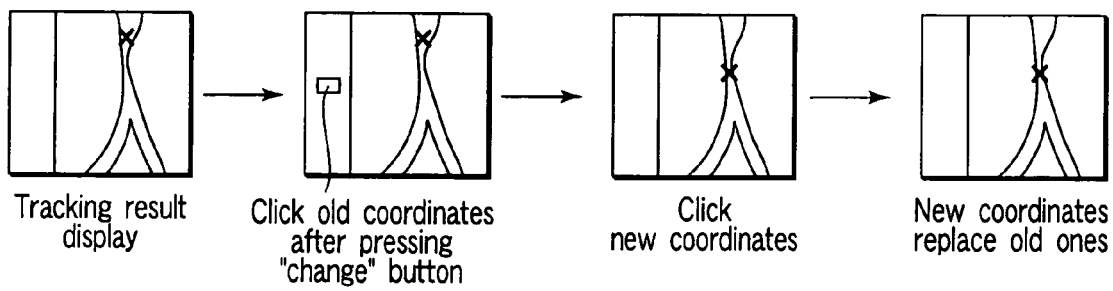
FIG. 38 is a view showing a procedure of correcting a tracking result in step S52 in FIG. 30.
Figure 39:
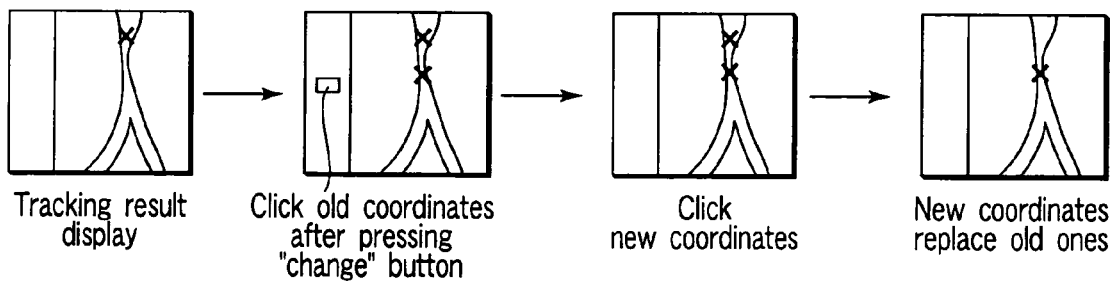
FIG. 39 is a view showing a procedure of correcting a tracking result in step S52 in FIG. 30.
Figure 40:
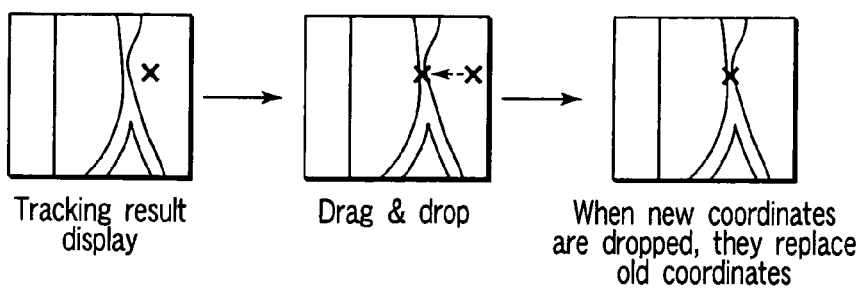
FIG. 40 is a view showing a procedure of correcting a tracking result in step S52 in FIG. 30.

The following is an operation method associated with correction of a tracking result, i.e., a change of the position of an extracted feature point. As shown in FIG. 37, when the operator clicks a desired position on an image with a mouse or the like, the old coordinates of a feature point disappear, and new coordinates replace the old ones. As shown in FIG. 38, when the operator clicks the change button, a tracked feature point becomes a target which can be corrected. When the operator clicks a correction target point in the target and clicks a desired position on the image with the mouse or the like, the old coordinates of the correction target point disappear, and new coordinates replace the old ones. As shown in FIG. 39, when the operator clicks the change button, clicks a desired position on the image with the mouse or the like, and further clicks a correction target point in the tracked feature point, the old coordinates of the correction target point disappear, and new coordinates replace the old ones. As shown in FIGS. 40 and 47, the operator drags and drops a correction target point in a tracked feature point from old coordinates to new coordinates.

In addition, it suffices to display a correction candidate. This apparatus displays a candidate with coordinates exhibiting the second or third highest correlation. Clicking the corresponding position will select the candidate. The apparatus displays the midpoint between preceding and succeeding frames as a candidate. Clicking the confirmation button will confirm the position of the feature point.

Figure 41:
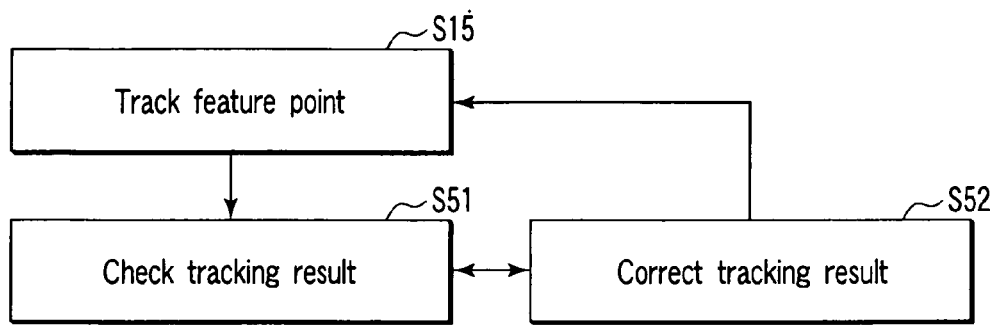
FIG. 41 is a view showing another correction procedure for tracking processing in FIG. 30.

As shown in FIG. 41, when the position of a feature point on a frame is corrected (S52), the process returns to tracking (S15) to execute tracking again on another frame near the corrected position. Upon checking the result of the tracking executed again and determining that it is necessary to correct the result, the operator also performs manual correcting operation for this frame.

Figure 42:
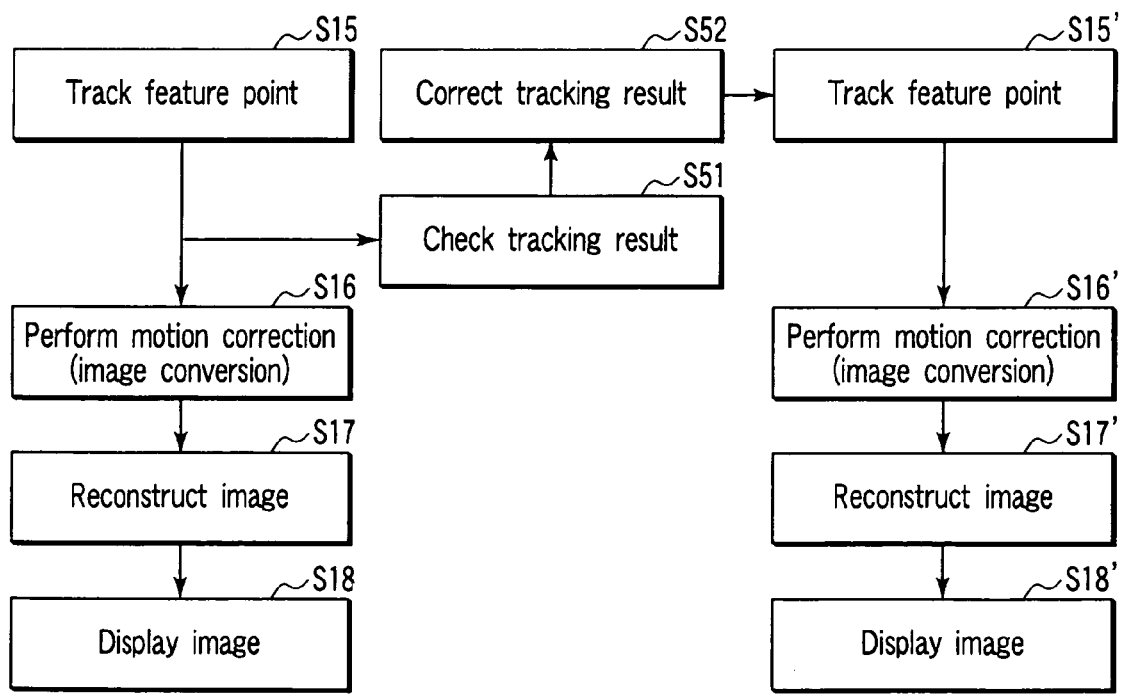
FIG. 42 is a view showing another example of using a tracking correction result in FIG. 30.

As shown in FIG. 42, it suffices to automatically perform motion correction processing (S16) from a tracking result, reconstruct a three dimensional image (S17), and display the image (S18) without checking and correcting the tracking result. On the other hand, the operator checks the display result of the three dimensional image (S51), and determines whether it is necessary to correct the result (S52). The apparatus then performs motion correction processing in accordance with the corrected tracking result (S16'), and reconstructs a three dimensional image by performing reconstruction processing (S17'), thereby displaying the three dimensional image with improved image quality (S18'). With this operation, the apparatus displays a reconstructed image with moderate image quality at high speed first, and then displays a reconstructed image with high image quality after correcting operation.

Figure 43:
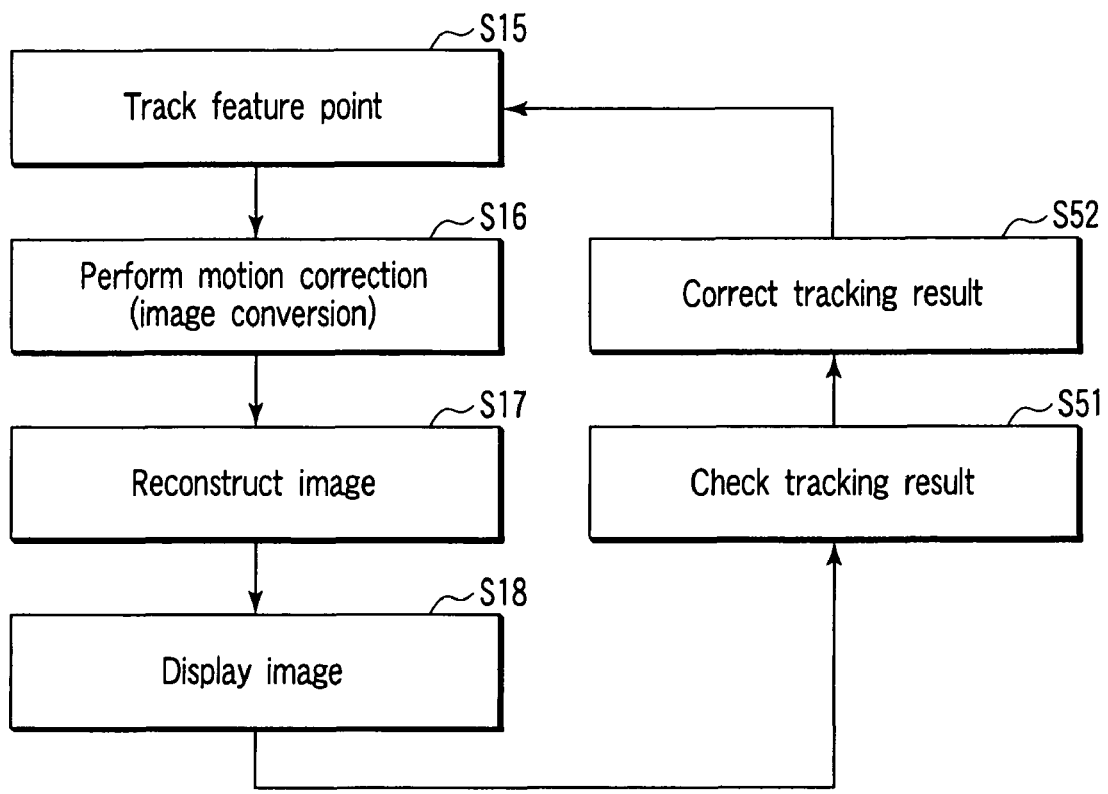
FIG. 43 is a view showing another example of using a tracking correction result in FIG. 30.

In addition, as shown in FIG. 43, the operator sees a reconstructed image first instead of checking a tracking result in the middle of the process. Upon determining that this image is not proper, the operator can use the apparatus to check (S51) and correct (S52) the tracking result.

As shown in FIG. 44, the feature point extraction unit 11 automatically diagnoses a tracking result. Upon determining that the result is not proper, the feature point extraction unit 11 displays a message for prompting the operator to increase the number of feature points, i.e., perform additional input operation (S53). In automatic diagnosis, as shown in FIG. 45, the feature point extraction unit 11 observes the correlation value between images, and determines that the tracking result is not proper, when the correlation value exceeds the threshold. In addition, the feature point extraction unit 11 observes the integral value of the correlation value between images, and determines that the tracking result is not proper, when the integral value exceeds the threshold. That is, when the correlation value between frames becomes equal to or smaller than the threshold, the feature point extraction unit 11 regards that results on the subsequent frames will include larger errors, and requires the operator to perform additional input operation at this frame. The feature point extraction unit 11 cumulatively adds the correlation values between frames. When the cumulated value at a given frame becomes equal to or more than a threshold, the feature point extraction unit 11 regards that results on the subsequent frames will include larger errors, and requires the operator to perform additional input operation at this frame. Upon determining that a tracking result is not proper, the feature point extraction unit 11 automatically displays a window for requiring the operator to perform additional input operation.

(Method of Radiographing X-ray Image)

Figure 48:
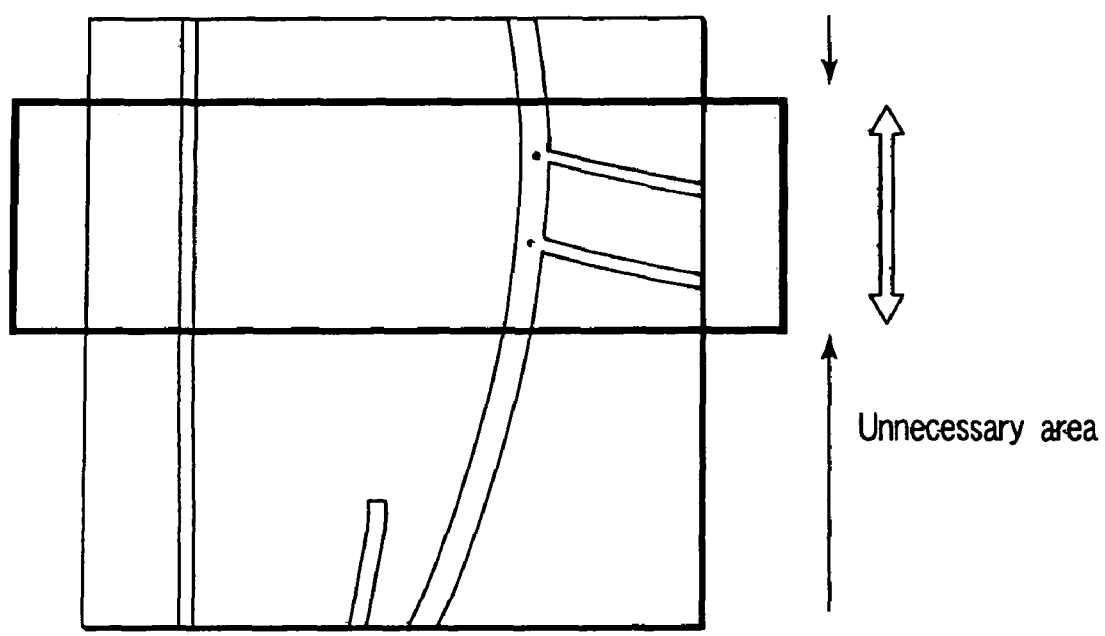
FIG. 48 is a view showing the narrowing range of an x-ray collimator by a radiography control unit in FIG. 1.
Figure 49:
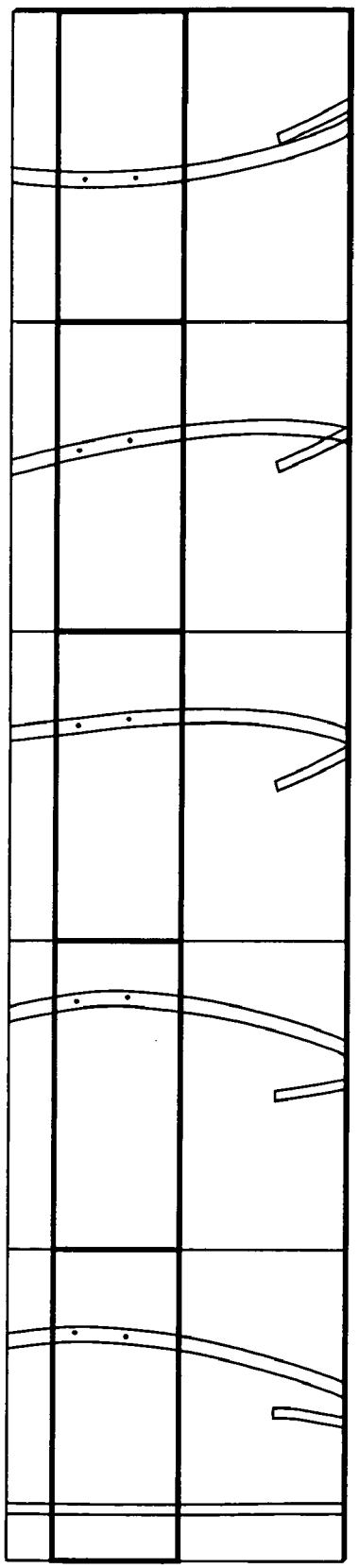
FIG. 49 is a view showing the narrowing range of the x-ray collimator by the radiography control unit FIG. 1 in a plurality of directions.
Figure 50:
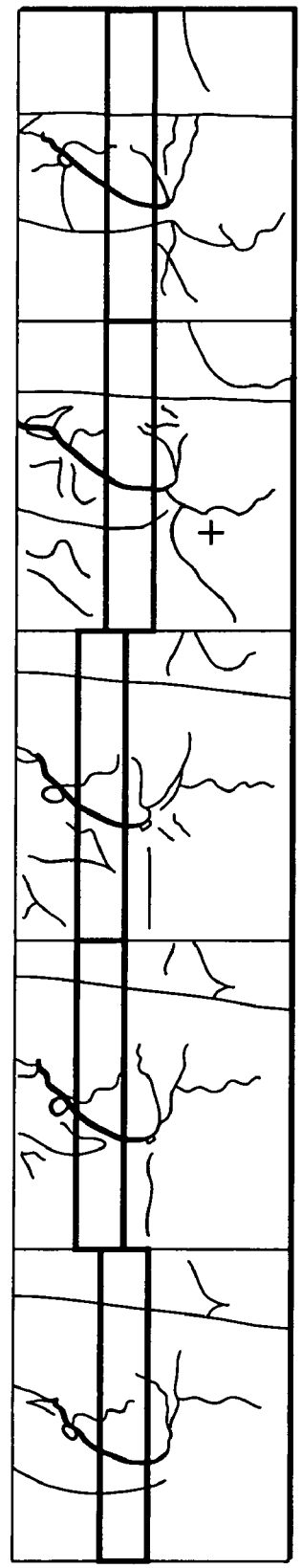
FIG. 50 is a view showing the narrowing range of the x-ray collimator by the radiography control unit FIG. 1 in a plurality of directions.

In the above rotational radiography, if, in particular, a region of interest (a portion of the subject) is small, limiting an X-ray irradiation field to the region of interest in the manner shown in FIG. 48 makes it possible to expect an exposure reducing effect. As shown in FIG. 49, a region of interest includes only the portion between the two black markers and its periphery. In this case, the lower half of each frame is subjected to useless exposure. In addition, as shown in FIG. 50, a region of interest includes only the portion between the two black markers and its periphery. In this case as well, the lower half of each frame is subjected to useless exposure. In addition, it is obvious that the position of the region of interest shifts in the Y direction upon rotation and motion.

As a method of reducing exposure in rotational radiography, the apparatus uses a method of setting a region of interest, and narrowing X-rays so as not to apply X-rays outside the region of interest. More specifically, a region of interest is designated by using one two dimensional image, and the apparatus performs rotational radiography upon narrowing X-rays within the region of interest. More specifically, a region of interest is designated by using one two dimensional image, and a moving region is set by tracking movement within the two dimensional image. The apparatus then performs rotational radiography upon narrowing X-rays within the moving region. This makes it possible to perform radiography while minimizing exposure. This operation will be described in detail below.

Figure 51:
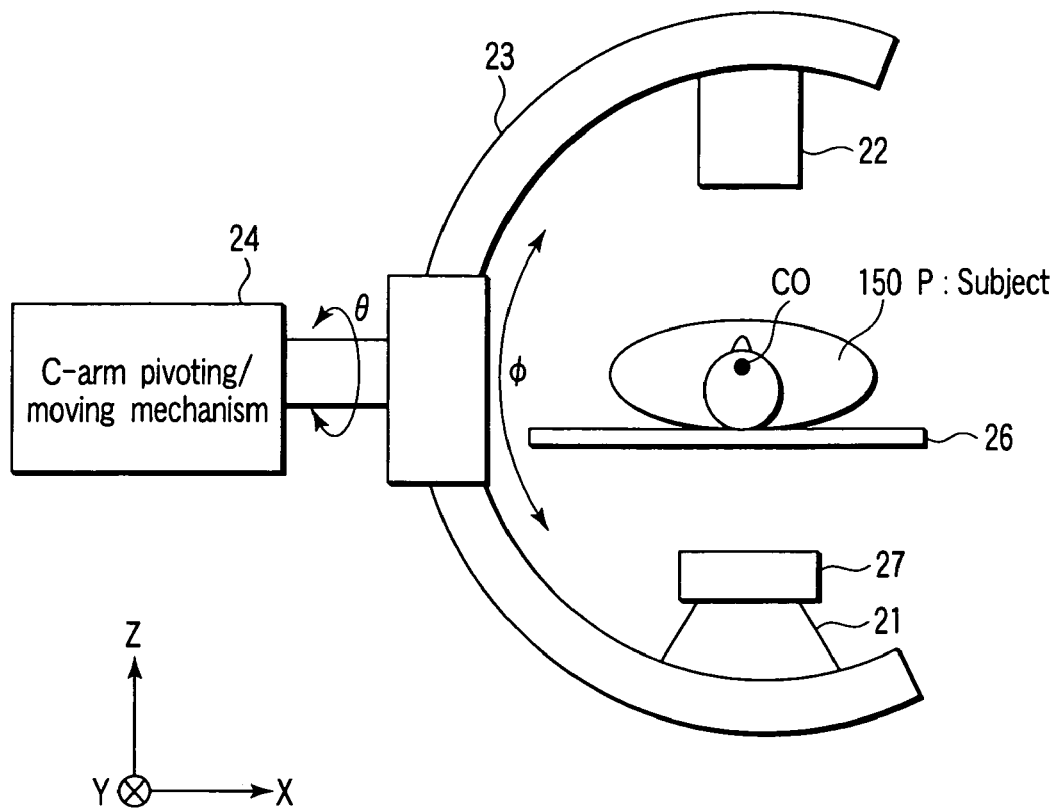
FIG. 51 is a view showing the rotational radiography angle of a C-arm in FIG. 1.
Figure 52:
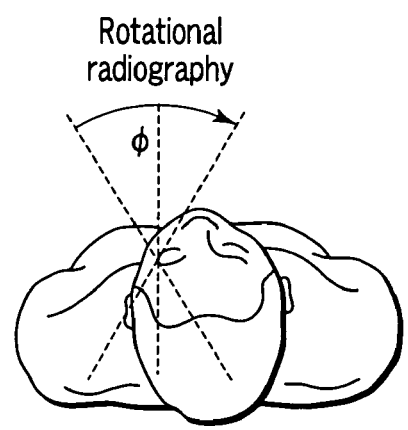
FIG. 52 is a view showing the rotational radiography angle of the C-arm in FIG. 52.

As shown in FIGS. 51 and 52, in rotational radiography, the C-arm 23 slides/rotates ($\phi$) and axially rotates ($\theta$), and the X-ray tube 21 and the X-ray detector 22 continuously rotate together. This apparatus repeats radiography during this period.

Figure 53:
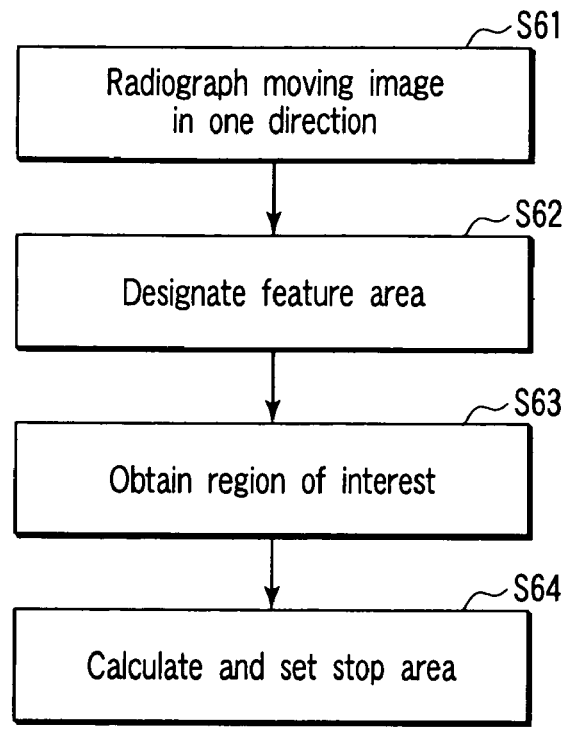
FIG. 53 is a view showing a procedure of determining a stop area by the radiography control unit in FIG. 1.

As shown in FIG. 53, the radiography control unit 2 fixes the X-ray tube 21 and the X-ray detector 22 at given positions and radiographs a moving image (S61). If a target is a blood vessel, contrast medium injection is required. If a target is an intracorporeal device such as a stent, no contrast medium injection is performed. This apparatus obtains a moving image by performing radiography corresponding to at least one heartbeat. A radiography rate is arbitrarily set, and is generally set to 7 to 30 fps in many cases. Of an acquired moving image, a given frame (the Nth frame) is displayed. The operator designates a feature point on this frame (S62). Assume that the operator designates one or a plurality of feature points. The computer set a feature region by providing a margin for a feature point. If, for example, the operator designates a region centered on a feature point with the mouse, the radiography control unit 2 stores, as a feature region, for example, a 31×31 region centered on the selected feature point coordinates.

Figure 54:
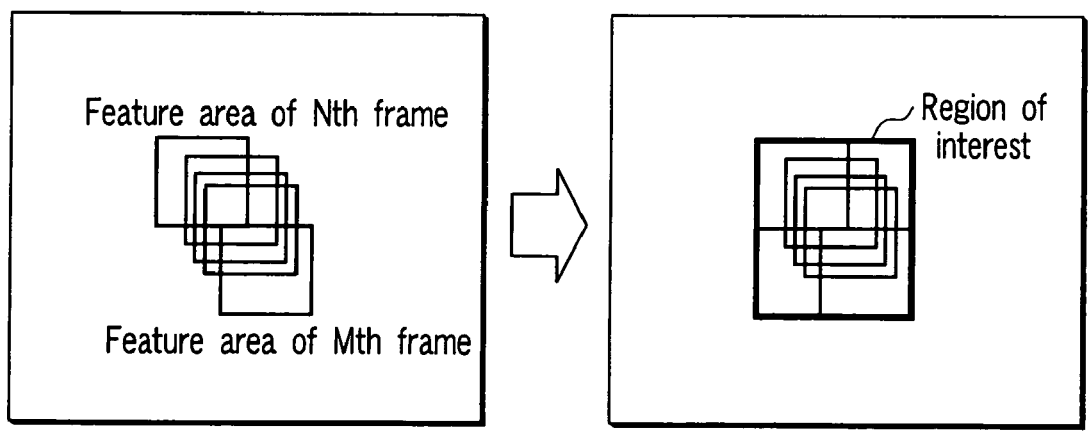
FIG. 54 is a supplementary view for explaining step S63 in FIG. 53.

The radiography control unit 2 searches an adjacent frame (the (N+1) frame) in the moving image for a place most similar to the feature region, e.g., a place having the maximum cross-correlation value. The radiography control unit 2 stores a 31×31 region centered on the detected place as a new feature region in the memory. The radiography control unit 2 then searches the (N+2)th frame for a place most similar to the feature region stored at the (N+1)th frame. Likewise, the radiography control unit 2 performs so-called tracking up to the Mth frame. The Nth frame and the Mth frame each include data corresponding to at least one heartbeat. As shown in FIG. 54, the radiography control unit 2 calculates the maximum range of movement from the Nth frame to the Mth frame, and sets it as a region of interest (S63).

Figure 55:
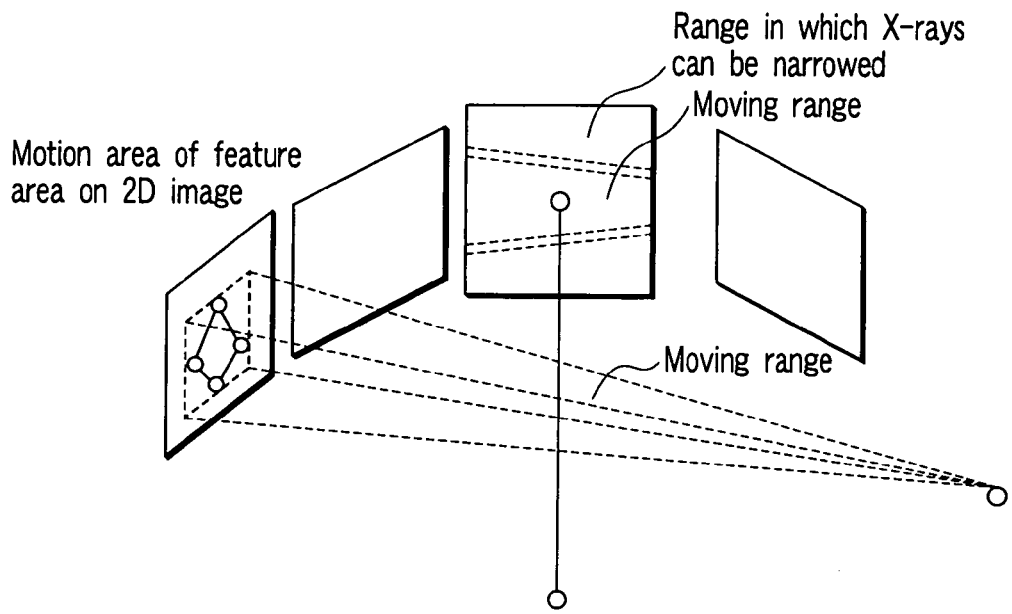
FIG. 55 is a supplementary view for explaining step S64 in FIG. 53.

The radiography control unit 2 calculates the aperture (stop region) of a stop 27 on the basis of the set region of interest. First of all, as shown in FIG. 55, the radiography control unit 2 projects a straight line connecting the region of interest and the X-ray tube 21 onto an image from another direction in rotational radiography. The straight line can be drawn as a line on a two dimensional image from another direction. This is generally epipolar geometry. The projected line will be called an epipolar line. As shown in FIG. 54, in the image from another direction, the epipolar line includes a range in which the subject moves, and it can be determined that the subject does not move into any region outside the epipolar line. Performing this calculation in all directions in which radiography is to be performed makes it possible to obtain a range within which the apparatus is allowed to narrow X-rays. The apparatus then performs rotational radiography while narrowing X-rays within the range obtained in this manner.

Figure 56:
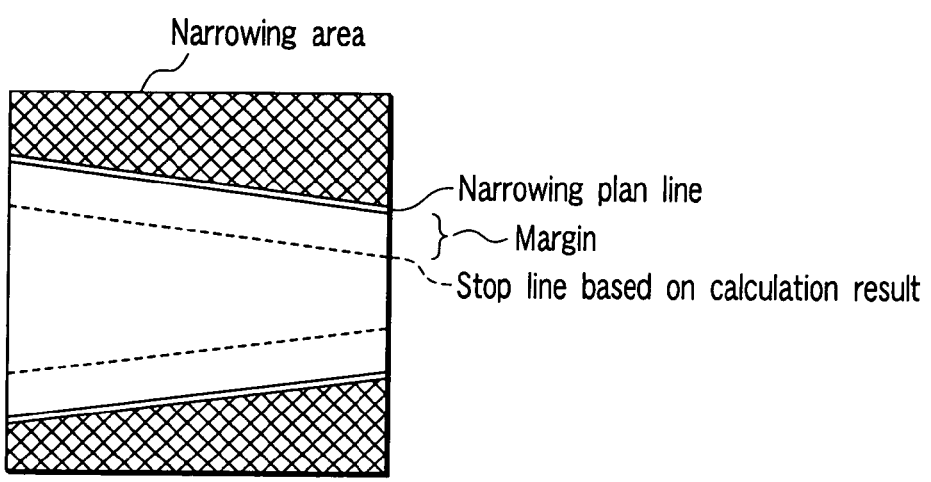
FIG. 56 is a view for explaining a method of determining a stop area in step S64 in FIG. 55.

As shown in FIG. 57, it is preferable to change the narrowing range for each radiographing direction (for each frame). As shown in FIG. 58, the apparatus may calculate a maximum region of interest which covers a region of interest in each radiographing direction, and fix the calculated range as a narrowing range common to all the radiographing directions. In the case of an organ which has periodicity but does not have perfectly periodic motion like the heart, as shown in FIG. 56, a slight margin should be provided for a region of interest to enlarge the region of interest, thereby determining a narrowing range.

Note that in the conventional cardiac reconstruction method, a feature point is designated, and tracking is performed for the feature point. According to the processing method proposed in this embodiment, a feature point has already been designated on a two dimensional image. In addition to feature point designation in the conventional method, the operator must designate the same feature point twice. This embodiment therefore reduces the number of times of designation to one. For this purpose, the apparatus uses the following technique. First of all, assume that the apparatus performs radiography of the first two dimensional image at the same angle as one of planned radiography angles at which rotational radiography is to be performed later. The apparatus executes two dimensional radiography and rotational radiography. The apparatus then extracts one image at the same angle as that of the two dimensional image from the images obtained by rotational radiography. The apparatus extracts an image at the same cardiac phase as that of one image extracted from the rotational images. The two images extracted in this manner are images at the same angle and same cardiac phase. The apparatus searches for most similar coordinates within one image extracted from the rotational images by using the feature region designated in two dimensional radiography as a template. The apparatus then determines the searched-out image as initial coordinates for cardiac motion correction tracking.

The above two dimensional tracking can be omitted. The operator sets a region of interest in an image (a moving image or still image) in one direction. The region of interest designated in this case corresponds to the above motion region. In practice, as shown in FIG. 59, for example, the operator sets a region covering a region which he/she wants to see by visual observation while seeing a moving image in one direction. This operation is the same as that in step S64 in FIG. 53. This technique can be used for both a still organ and a moving organ.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A three dimensional image processing apparatus, comprising:
a storage unit which stores data of a plurality of images having different radiographing directions;
a feature point designation unit which designates, with operation by an operator, a respective feature point on at least two selected images selected from said plurality of images;
an operation support unit which generates information for supporting the operation of the operator to designate the respective feature points, wherein the operation support unit determines a predictive area in which a feature point on another selected image of the at least two selected images is located, on the basis of a two dimensional position of a feature point designated on at least one selected image of the at least two selected images and a radiographing direction of the another selected image;
a three dimensional position calculation unit which calculates a three dimensional position associated with the respective feature points on the basis of (1) a radiographing direction corresponding to the at least two selected images, and (2) two dimensional positions of the designated respective feature points on the at least two selected images;
a two dimensional position calculation unit which calculates a two dimensional position of a calculated feature point on an unselected image of said plurality of images on the basis of (1) a radiographing direction corresponding to the unselected image, and (2) the calculated three dimensional position of the respective designated feature points;
a feature point extraction unit which extracts an extracted feature point from the unselected image;
a positional shift calculation unit which calculates a positional shift of a two dimensional position of the extracted feature point with respect to the calculated two dimensional position of the calculated feature point;
a correction unit which corrects a position of the unselected image on the basis of the calculated positional shift; and
an image reconstruction unit which reconstructs a three dimensional image on the basis of the at least two selected images and the corrected unselected image.

2. The three dimensional image processing apparatus according to claim 1, wherein the operation support unit displays the determined predictive area together with the another selected image.

3. The three dimensional image processing apparatus according to claim 1, wherein the selected images correspond to a same cardiac phase.

4. The three dimensional image processing apparatus according to claim 1, wherein the operation support unit calculates a predictive position of the feature point on the another selected image on the basis of the radiographing direction corresponding to the another selected image and a plurality of two dimensional positions associated with the respective feature points designated on said at least two selected images.

5. The three dimensional image processing apparatus according to claim 1, wherein the operation support unit calculates a predictive position of a feature point on the another selected image on the basis of the radiographing direction corresponding to the another selected image and a plurality of two dimensional positions associated with the respective feature points designated on said at least two selected images, and superimposes and displays a mark representing the predictive position or a mark representing a predictive area including the predictive position on the another selected image.

6. The three dimensional image processing apparatus according to claim 1, wherein the operation support unit calculates a predictive line of the feature point on the another selected image on the basis of the radiographing direction corresponding to the another selected image and a plurality of two dimensional positions associated with the respective feature points designated on said at least two selected images, and superimposes and displays a mark representing the predictive line or a mark representing a predictive area including the predictive line on the another selected image.

7. The three dimensional image processing apparatus according to claim 1, wherein the operation support unit specifies a blood vessel area from said at least two selected images, and superimposes and displays a mark representing a blood vessel center line or a blood vessel model on the another selected image on the basis of the blood vessel area.

8. The three dimensional image processing apparatus according to claim 1, wherein the operation support unit generates a warning when a position of a feature point designated on the another selected image in accordance with operation by an operator falls outside the predictive area.

9. The three dimensional image processing apparatus according to claim 1, wherein the operation support unit displays a message which prompts a change of the at least two selected images when projection lines to the respective feature points designated on said at least two selected images separate from each other by a predetermined distance.

10. The three dimensional image processing apparatus according to claim 1, further comprising an image processing unit which performs image processing for the at least two selected images.

11. The three dimensional image processing apparatus according to claim 10, wherein the image processing unit converts a density of the at least two selected images.

12. The three dimensional image processing apparatus according to claim 1, further comprising an image processing unit which enlarges the at least two selected images, and a display unit which displays the enlarged selected images with a focus on the designated feature point.

13. The three dimensional image processing apparatus according to claim 1, further comprising a display unit which displays a single selected image on which a feature point has been designated, together with a selected image on which a feature point has not been designated.

14. The three dimensional image processing apparatus according to claim 1, further comprising a display unit which displays a plurality of selected images on which feature points have been designated, together with a selected image on which a feature point has not been designated.

15. An X ray diagnosis apparatus including a three dimensional image processing apparatus defined in claim 1, comprising:
an X ray tube which generates X rays;
an X-ray collimator which variably narrows X rays from the X ray tube;
an X ray detector which detects X rays transmitted through a subject;
a rotating mechanism which rotates the X ray tube around the subject together with the X ray detector;
a region of interest setting unit which sets a region of interest on an image of at least one frame by the X ray detector; and
a control unit which controls an opening degree of the x-ray collimator on the basis of the set region of interest.

16. A three dimensional image processing apparatus, comprising:
a storage unit which stores data of a plurality of images having different radiographing directions;
a feature point designation unit which designates, with operation by an operator, a respective feature point on at least two selected images selected from said plurality of images;
a three dimensional position calculation unit which calculates a three dimensional position associated with the respective feature points on the basis of (1) a radiographing direction corresponding to the at least two selected images, and (2) two dimensional positions of the designated respective feature points on the selected images;
a two dimensional position calculation unit which calculates a two dimensional position of a calculated feature point on an unselected image of said plurality of images on the basis of (1) a radiographing direction corresponding to the unselected image, and (2) the calculated three dimensional position of the respective designated feature points;
a feature point extraction unit which extracts an extracted feature point from the unselected image;
a display unit which displays a feature point extraction result obtained by the feature point extraction unit, wherein the display unit displays a graph representing a change in coordinates of the extracted feature point extracted by the feature point extraction unit;
a positional shift calculation unit which calculates a positional shift of a two dimensional position of the extracted feature point with respect to the calculated two dimensional position of the calculated feature point;
a correction unit which corrects a position of the unselected image on the basis of the calculated positional shift; and
an image reconstruction unit which reconstructs a three dimensional image on the basis of the at least two selected images and the corrected unselected image.

17. The three dimensional image processing apparatus according to claim 16, wherein the display unit superimposes and displays one of a dot mark, a circular mark, a crosshair mark, and a rectangular mark representing the extracted feature point extracted by the feature point extraction unit on the unselected image.

18. The three dimensional image processing apparatus according to claim 16, wherein the display unit superimposes and displays the extracted feature point extracted by the feature point extraction unit on the unselected image, together with a feature point extracted from another unselected image.

19. The three dimensional image processing apparatus according to claim 16, wherein the display unit enlarges and displays the unselected image with a focus on the extracted feature point extracted by the feature point extraction unit.

20. The three dimensional image processing apparatus according to claim 16, wherein the display unit displays a plurality of feature points extracted from a plurality of unselected images by the feature point extraction unit, together with said plurality of unselected images.

21. The three dimensional image processing apparatus according to claim 16, further comprising an operation unit configured to perform a correcting operation for a position of the extracted feature point extracted by the feature point extraction unit.

22. The three dimensional image processing apparatus according to claim 21, wherein the image reconstruction unit reconstructs a first three dimensional image on the basis of the unselected image whose position is corrected in accordance with the positional shift calculated from the extracted feature point extracted by the feature point extraction unit and the at least two selected images, and reconstructs a second three dimensional image on the basis of an unselected image whose position is corrected in accordance with a positional shift calculated from the feature point corrected and extracted by the operation unit and the at least two selected images.

23. The three dimensional image processing apparatus according to claim 16, further comprising a determination unit which determines on the basis of a correlation value between unselected images whether the extracted feature point extracted by the feature point extraction unit is adapted to be added.

24. An X ray diagnosis apparatus including a three dimensional image processing apparatus defined in claim 16, comprising:
   an X ray tube which generates X rays;
   an X-ray collimator which variably narrows X rays from the X ray tube;
   an X ray detector which detects X rays transmitted through a subject;
   a rotating mechanism which rotates the X ray tube around the subject together with the X ray detector;
   a region of interest setting unit which sets a region of interest on an image of at least one frame by the X ray detector; and
   a control unit which controls an opening degree of the x-ray collimator on the basis of the set region of interest.

* * * * *